(12) United States Patent
Nigam et al.

(10) Patent No.: US 8,460,929 B2
(45) Date of Patent: Jun. 11, 2013

(54) METHODS OF TISSUE GENERATION AND TISSUE ENGINEERED COMPOSITIONS

(75) Inventors: Sanjay Kumar Nigam, Del Mar, CA (US); Eran Rosines, Virginia Beach, VA (US)

(73) Assignee: The Regents of the University of California, Oakland, CA (US)

(*) Notice: Subject to any disclaimer, the term of this patent is extended or adjusted under 35 U.S.C. 154(b) by 110 days.

(21) Appl. No.: 12/663,170

(22) PCT Filed: Jun. 4, 2008

(86) PCT No.: PCT/US2008/065818
§ 371 (c)(1), (2), (4) Date: Sep. 29, 2010

(87) PCT Pub. No.: WO2008/151254
PCT Pub. Date: Dec. 11, 2008

(65) Prior Publication Data
US 2011/0008892 A1    Jan. 13, 2011

Related U.S. Application Data

(60) Provisional application No. 60/941,934, filed on Jun. 4, 2007.

(51) Int. Cl.
*C12N 5/00* (2006.01)
*A01N 63/00* (2006.01)

(52) U.S. Cl.
USPC .............. 435/377; 424/93.7; 435/405

(58) Field of Classification Search
None
See application file for complete search history.

(56) References Cited

U.S. PATENT DOCUMENTS

2003/0166274 A1    9/2003    Hewitt et al.
2005/0074875 A1*   4/2005    Nigam et al. ............. 435/366

FOREIGN PATENT DOCUMENTS

WO        03045226 A2    6/2003

OTHER PUBLICATIONS

Bush et al. Development and differentiation of the ureteric bud into the ureter in the absence of a kidney collecting system, Developmental Biology 298 (2006) 571-584.*

* cited by examiner

*Primary Examiner* — James Ketter
*Assistant Examiner* — Reza Ghafoorian
(74) *Attorney, Agent, or Firm* — Josephy R. Baker, Jr.; Gavrilovich, Dodd & Lindsey LLP

(57) ABSTRACT

Provided are methods and compositions for constructing stable mammalian embryonic epithelial tissues and organs as well as constructing kidney tissue, and treating renal failure. Disclosed are methods of using an active epithelial growth factor having the capability of effectuating induction of growth and morphogenesis is cells.

2 Claims, 8 Drawing Sheets

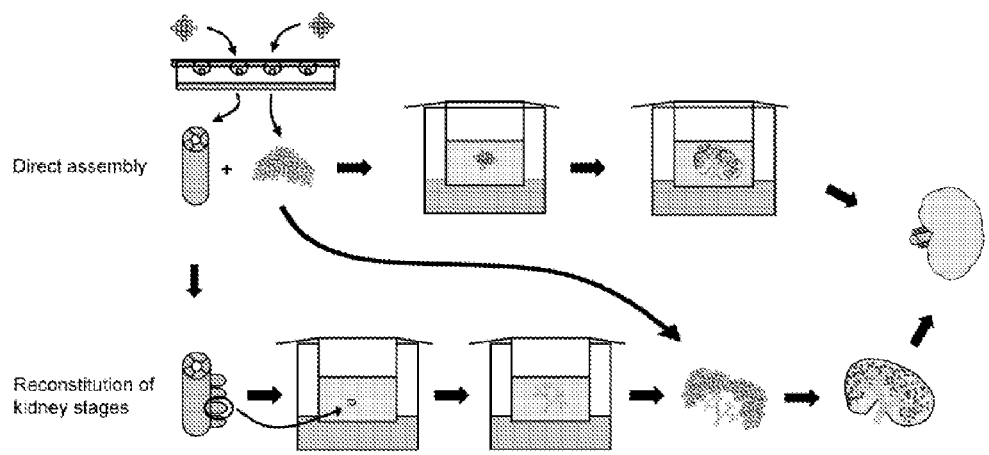
FIGURE 9A
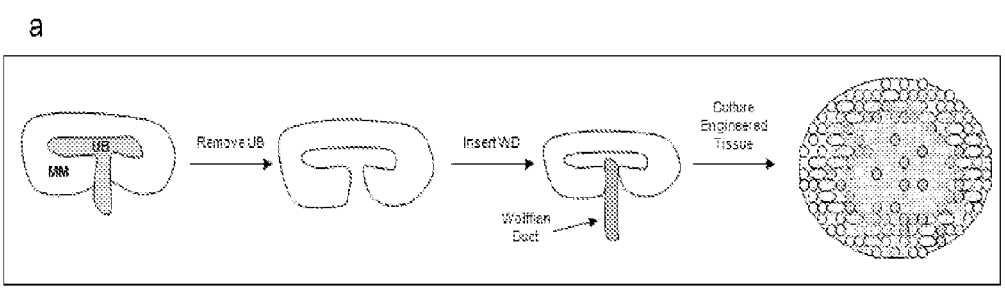
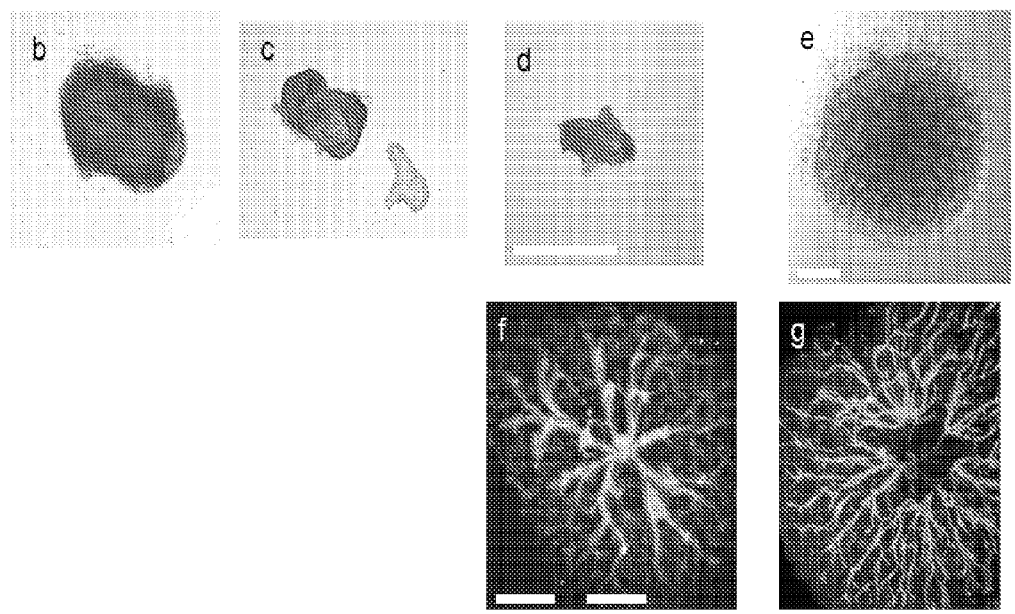
FIGURE 9B

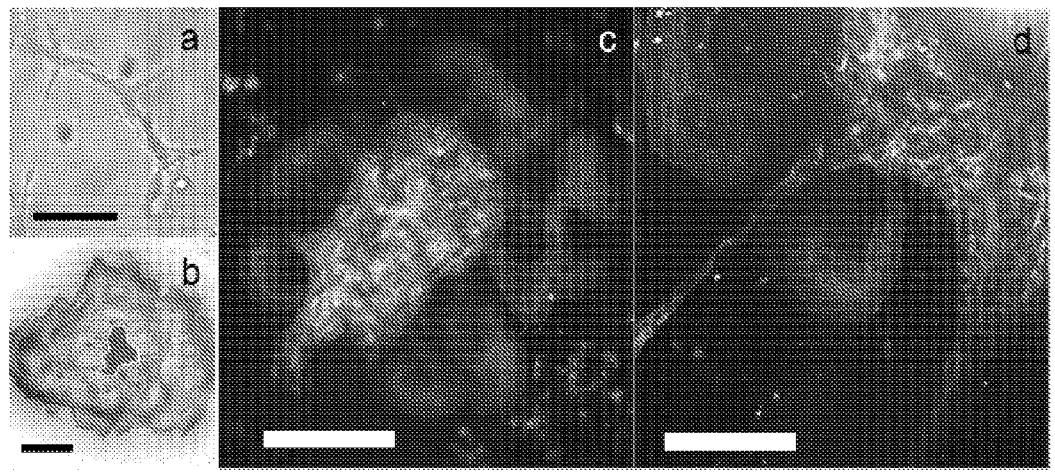
FIGURE 10A-D
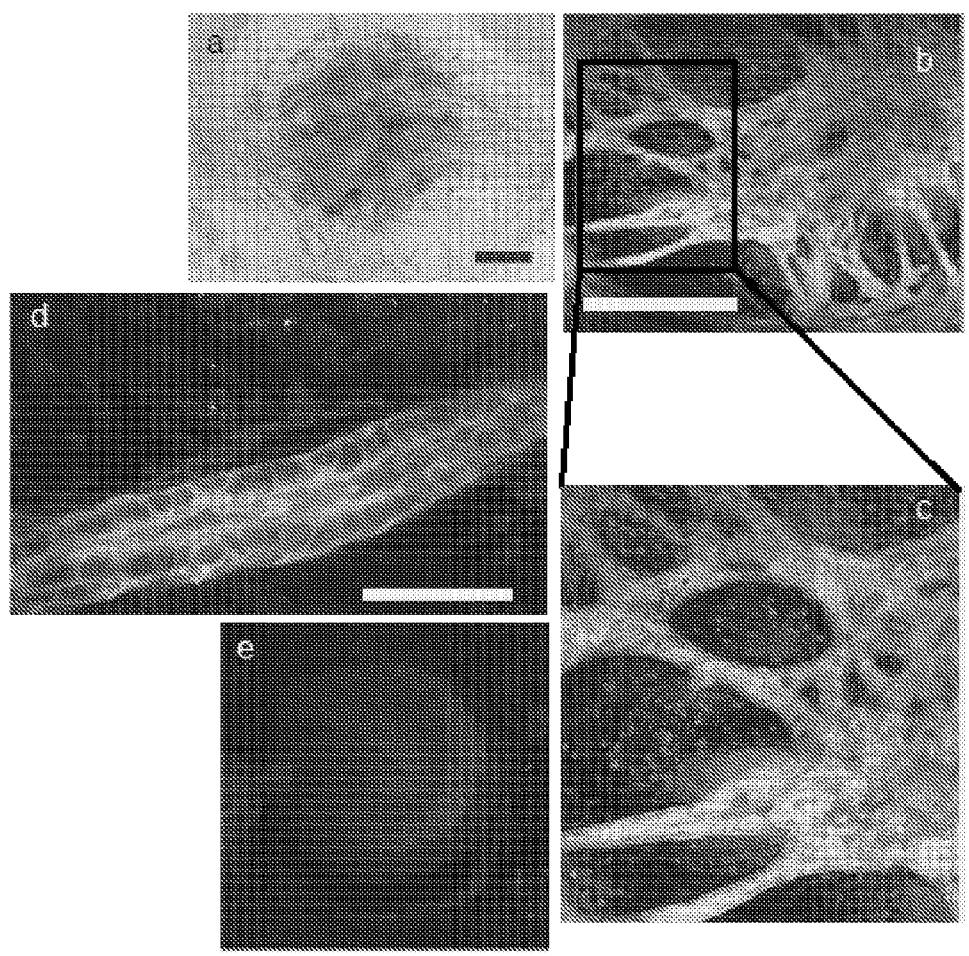
FIGURE 11

METHODS OF TISSUE GENERATION AND TISSUE ENGINEERED COMPOSITIONS

CROSS REFERENCE TO RELATED APPLICATIONS

This application is a U.S. National Stage Application filed under 35 U.S.C. 371 and claims priority to International Application No. PCT/US08/65818, filed Jun. 4, 2008, which application claims priority under 35 U.S.C. §119 to U.S. Provisional Application Ser. No. 60/941,934, filed Jun. 4, 2007, the disclosures of which are incorporated herein by reference.

FIELD OF THE INVENTION

The invention generally concerns methods of tissue engineering, and more particularly relates to methods and compositions for tubular tissue generation and more particularly to kidney tissue generation and replacement.

BACKGROUND

End-stage renal disease (ESRD) affects almost 350,000 people living in the United States with an incidence that has increased by over 50% in the past decade. Total Medicare expenditures on patients with ESRD exceed $11.3 billion (U.S. Renal Data Service: 2001 Annual Data Report: Atlas of End-Stage Renal Disease in the United States. Bethesda NIH, NIDDKD, 2001). The two current treatment modalities for ESRD, dialysis and transplantation, both have significant limitations. Patients on dialysis have an extremely high mortality rate, approaching 20% per year. Patient survival is markedly improved with renal transplantation; however, the number of renal transplants is severely limited by the short supply of available organs and many patients die while awaiting transplantation of a kidney allograft.

SUMMARY

The disclosure provides a stepwise in vitro method of engineering kidney-like tissues capable of being implanted, recruiting a vasculature and developing glomeruli. Using a reconstitution approach based, in part, upon the fact that stages of kidney development are separable in vitro, the disclosure provides an approach to sequentially induce an epithelial tubule (e.g., the Wolffian duct (WD)), to undergo in vitro budding, combining bud/metanephric mesenchyme and implantation of the combined tissue that results in vascularization. The disclosure demonstrates that tubular tissues can be stimulated in vitro to reproduce kidney formation with appropriate spatial relationships of nephrons in a stepwise fashion resulting in an in vitro tissue that can be implanted in host recipients, thereby recruiting vascularized glomeruli. Exclusive optimization studies of growth factor and matrix (natural and artificial) conditions indicate multiple suitable combinations and suggest both a robust and a minimal system. A whole genome microarray analysis was performed on the recombined tissue to verify that the tissue was recapitulating gene expression changes that occur in vivo during later stages of kidney development.

The disclosure provides a method for in vitro engineering and constructing a mammalian kidney. The method includes separating ureteric bud, Wolffian duct bud, or ureteric and Wolffian duct bud (UB, WD, or UB and WD) tissue from mesenchyme tissue obtained from an embryonic kidney rudiment; culturing the isolated ureteric bud, Wolffian duct bud, or ureteric and Wolffian duct bud tissue in a biocompatible matrix in the presence of a culture medium comprising pleiotrophin and/or heregulin or an active fragment thereof for a sufficient time and under sufficient conditions to produce tubular branches within the biocompatible matrix; separating the tubular branches to obtain a plurality of bud fragments; culturing each of the bud fragments in a biocompatible matrix with a culture medium comprising pleiotrophin and/or heregulin or an active fragment thereof to generate a plurality of tissues comprising tubular branches; combining the plurality of tissues comprising tubular branches with metanephric mesenchyme (MM) tissue in the presence of nutrient medium comprising pleiotrophin, heregulin, a combination of pleotrophin and heregulin or an active fragment of the foregoing alone or in combination; and culturing the UB, WD, or UB and WD and MM under conditions sufficient to cause the MM to differentiate and form nephron structures thereby forming a kidney.

The disclosure provides a functional mammalian kidney engineered and constructed in vitro, comprising: a ureteric bud, Wolffian duct bud, or ureteric and Wolffian duct bud (UB, WD, or UB and WD) tissue propagated in culture in the presence of a composition comprising pleiotrophin, heregulin, a combination of pleotrophin and heregulin or an active fragment of the foregoing alone or in combination to produce a functioning tubular structures; and a metanephric mesenchyme (MM) tissue propagated from cultured embryonic mesenchymal tissue fragments or cells to produce functioning nephrons wherein the ureteric bud, Wolffian duct bud, or ureteric and Wolffian duct bud tissue and the metanephric mesenchyme are co-cultured and wherein the ureteric bud, Wolffian duct bud, or ureteric and Wolffian duct bud tissue induces the metanephric mesenchyme to form nephrons, thereby forming a functional mammalian kidney.

The disclosure provides a method of propagating ureteric bud (UB), Wolffian duct bud (WD), or ureteric and Wolffian duct bud cells in culture. The method includes culturing a UB, WD, or UB and WD in vitro under conditions that induce the UB, WD, or UB and WD to undergo branching morphogenesis to generate a population of UBs, WDs, or UBs and WDs comprising tubular branches; subdividing the UB, WD, or UB and WD population; and resuspending each subpopulation in culture media.

The disclosure also provides a method for in vitro culturing and propagating ureteric bud, Wolffian duct bud, or ureteric and Wolffian duct bud tissue. The method includes isolating ureteric bud, Wolffian duct bud, or ureteric and Wolffian duct bud tissue from mesenchyme tissue obtained from embryonic kidney rudiments; culturing the isolated ureteric bud, Wolffian duct bud, or ureteric and Wolffian duct bud tissue in a biocompatible matrix in the presence of a culture medium comprising pleiotrophin, heregulin, a combination of pleotrophin and heregulin or an active fragment of the foregoing alone or in combination for a sufficient time and under sufficient conditions to product tubular branches within the biocompatible matrix; separating the plurality of branch tips to generate bud fragments; and culturing each of the bud fragments in a biocompatible matrix with a culture medium comprising pleiotrophin, heregulin, a combination of pleotrophin and heregulin or an active fragment of the foregoing alone or in combination.

The disclosure also provides a method for growing renal tubule cells in vitro, comprising culturing kidney cells in a growth medium comprising pleiotrophin, heregulin, a combination of pleotrophin and heregulin or an active fragment of the foregoing alone or in combination in an amount effective for achieving tubulogenesis.

The disclosure further provides a method for stimulating epithelial organogenesis, by contacting an epithelial tissue with an effective amount of a composition comprising one or more mesenchymally derived growth factor(s) secreted by mesenchymal tissue in culture; and culturing the epithelial tissue and the composition for a sufficient period of time and under conditions to allow the tissue and the composition to interact, wherein the composition stimulates epithelial organogenesis.

The disclosure also provides in vitro tissue generated by the foregoing method.

The disclosure includes a method of stimulating branching morphogenesis in an epithelial tissue comprising contacting the epithelial tissue with a composition comprising pleiotrophin and/or heregulin.

The disclosure provides a method for in vitro tissue engineering of a functional mammalian epithelial tissue, organ or a fragment thereof by culturing and propagating embryonic epithelial explant, tissues, and/or cells by isolating the explant, tissue, and/or cells and growing the explant, tissue, and/or cells in a culture medium comprising pleiotrophin, heregulin, a combination of pleotrophin and heregulin or an active fragment of the foregoing alone or in combination, permitting the culture to form multiple branches, dissecting out individual tips of the branches; reculturing the branch tips in the culture medium comprising a heparin binding molecule (e.g., pleiotrophin, heregulin, a combination of pleotrophin and heregulin or an active fragment of the foregoing alone or in combination); combining the branch tips with embryonic or fetal mesenchymal tissue and/or cells, in the presence of the mixture of a culture medium in or on a biocompatible substrate; and culturing the combination in culture medium conditions suitable for tissue growth and tubulogenesis.

The disclosure further provides a method for stimulating branching morphogenesis in a kidney cell culture. The method includes contacting the kidney cell culture with an effective amount of a composition comprising one or more mesenchymally derived growth factor(s) secreted by a mesenchyme tissue in culture; and culturing the kidney cell culture and the composition for a sufficient period of time and under conditions to allow the cells and the composition to interact, wherein the composition stimulates branching tubular morphogenesis.

The disclosure also provides in vitro engineered kidney tissue. In one aspect of the disclosure the in vitro engineered kidney tissue is generated by the methods as described herein.

Also provided by the disclosure is a method of in vitro culturing and propagating metanephric mesenchyme tissue, comprising: isolating mesenchyme tissue at the time of induction; culturing the mesenchymal tissue in a composition comprising serum, nutrient rich medium, and mesenchymal and/or ureteric bud, Wolffian duct bud, or ureteric and Wolffian duct bud cell conditioned medium; and partitioning the cultured mesenchyme into multiple pieces and growing each piece separately in culture.

The disclosure also provide a genetically engineered mammalian kidney produced by culturing a population of cells comprising ureteric bud, Wolffian duct bud, or ureteric and Wolffian duct bud (UB, WD, or UB and WD) cells in a biocompatible matrix in the presence of a culture medium comprising pleiotrophin and/or heregulin or an active fragment thereof for a sufficient time and under sufficient conditions to produce tubular branches within the biocompatible matrix, and wherein at least one ureteric bud, Wolffian duct bud, or ureteric and Wolffian duct bud cell of the population of cells is transfected with an exogenous polynucleotide such that the exogenous polynucleotide expresses a product; separating the tubular branches to obtain a plurality of bud fragments; culturing each of the bud fragments in a biocompatible matrix with a culture medium comprising pleiotrophin and/or heregulin or an active fragment thereof to generate a plurality of tissues comprising tubular branches; combining the plurality of tissues comprising tubular branches with metanephric mesenchyme (MM) tissue in the presence of nutrient medium comprising pleiotrophin and/or heregulin; and culturing the UB, WD, or UB and WD and MM under conditions sufficient to cause the MM to differentiate and form nephron structures thereby forming a kidney.

The disclosure provides a method of treating a subject suffering from kidney failure comprising transplanting a tissue-engineered kidney of the invention into a subject.

The disclosure also includes a method for treating acute renal failure (ARF) comprising administering to a subject suffering from ARF with a pharmaceutically effective amount of a composition comprising pleiotrophin, heregulin, a combination of pleotrophin and heregulin or an active fragment of the foregoing alone or in combination such that a symptom of ARF is ameliorated.

The disclosure also includes a renal tubule cell produced by culturing ureteric bud, Wolffian duct bud, or ureteric and Wolffian duct bud cells in a culture medium comprising pleiotrophin and/or heregulin in an amount effective for achieving tubulogenesis.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 9A-B shows another general in vitro kidney engineering strategy. (B) Schematic of the procedure followed in engineering kidney tissue from the Wolffian duct and MM. (B-G) Photomicrographs of the engineered tissues. (B) Whole embryonic day 13 rat kidney. (C) Kidney which has been separated into isolated UB and isolated MM. (D) Isolated MM from c, in which a piece of WD has been used to replace the UB. (E) After 7 days, the WD/MM co-culture grew similar to traditional in vitro kidney culture. (F-G) Confocal fluorescent micrographs of the engineered kidney tissue after 7 (f) and 12 (g) days of culture. (f; bright=DB lectin, UB derived tissues; faint=E-Cadherin, UB and MM derived epithelial tissues; g: PNA lectin staining (faint) revealed differentiation of glomerular podocytes). (300 μm scale bar).

FIGS. 10A-D shows UB cell aggregate co-culture with MM. Photomicrographs showing the recombination of cultured UB cells with freshly isolated MM. (A) Phase contrast of a 3D culture of UB cells. UB cells will form branching tubular structures when cultured in the appropriate matrix and with the appropriate growth factors. (B) Hanging drop aggregate of UB cells (outlined in yellow) surrounded by numerous freshly isolated MMs. (C-D) Confocal fluorescent photomicrograph of recombined tissue after 7 days of growth in culture. UBs are stained (*D. biflorus*) and both UB and MM derived polarized epithelial cells were stained (E-Cadherin) (C) (400 μm scale bar—A-C). d. Higher magnification examination of the recombined tissue showing that the MM derived tubule is continuous with the green UB cells—25 μm scale bar.

FIGS. 11A-D shows IMCD cell aggregate co-culture with MM. After 7 days, the IMCD cells organized into epithelial tubules, however MM induction did not appear very widespread (a). Cytokeratin staining (green) demonstrates that the IMCD cell aggregate formed tubular structures with lumens (b,c,d). While MM induction did not occur as strongly as with the UB cell aggregate, occasional comma shaped bodies (evident by PAX-2 staining, red) indicated mesenchymal- to epithelial-transformation could be induced by the IMCD cell aggregate (e) (400 μm scale bar—a,b; 50 μm scale bar—c,d).

DETAILED DESCRIPTION

Figure 1:
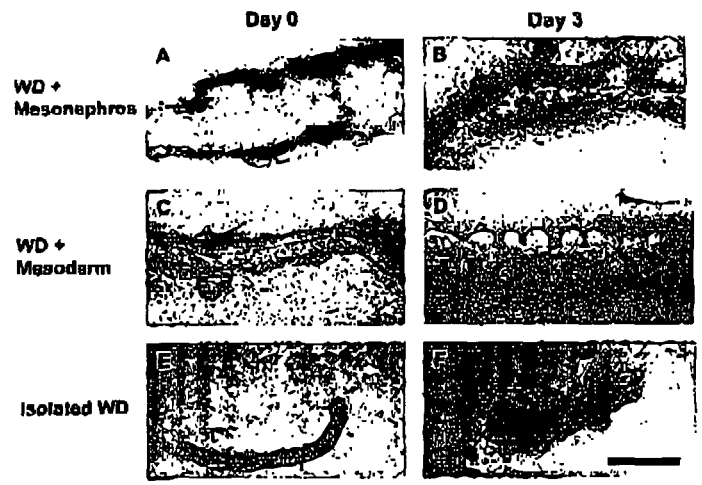
FIGS. 1A-F shows a Wolffian duct budding systems. The whole mesonephros (A, B), the Wolffian duct with a thin layer of intermediate mesoderm (C, D), and the Wolffian duct void of all other cell layers (E, F) can all be induced to bud according to the conditions outlined in Table 1. Scale bar corresponds to 500 µm.

As used herein and in the appended claims, the singular forms "a," "and," and "the" include plural referents unless the context clearly dictates otherwise. Thus, for example, reference to "a protein" includes a plurality of such proteins and reference to "the cell" includes reference to one or more cells known to those skilled in the art, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

The publications discussed above and throughout the text are provided solely for their disclosure prior to the filing date of the present application. Nothing herein is to be construed as an admission that the inventors are not entitled to antedate such disclosure by virtue of prior disclosure.

As used herein, the abbreviation UB, WD, or UB and WD includes ureteric bud, Wolffian duct bud, or ureteric and Wolffian duct bud cells obtained from UB, WD, or UB and WD tissue, as well as UB, WD, or UB and WD tissue fragments, whole UB, WD, or UB and WD tissue, and UB, WD, or UB and WD cell lines, unless clearly indicated otherwise in the specification. The UB, WD, or UB and WD cells may be primary cells obtained from embryonic kidney tissue by various techniques known in the art. Such primary UB, WD, or UB and WD cells are not immortalized (e.g., by SV40), but may be transfected and/or transformed to express a desired product, as discussed in more detail herein.

The culture system and methods of the disclosure provide the ability to propagate the isolated UB, WD, or UB and WD in vitro through several generations. For example, isolated stem cells, UB, WD, or any combination thereof are cultured in vitro and induced to undergo branching morphogenesis in the presence of BSN-CM or pleiotrophin and GDNF or pleiotrophin, FGF1, and GDNF. Following propagation of the buds, the propagated buds can be recombined with metanephric mesenchyme (MM) to induce nephron tissue formation. The tissue can then undergo vascularization in vivo upon implantation within the kidney of a subject. Using the various component pieces a functional kidney can be obtained. The disclosure provides a cell-based kidney development strategy. Unlike prior strategies, which have used tissue segments and recombination, the present disclosure demonstrates the ability to develop tissue components from substantially homogenous cell types followed by recombination of the tissue components. In one aspect, stem cells are useful as the initial cell type used in the methods of the disclosure.

The term "precursor cell," "progenitor cell," and "stem cell" are used interchangeably in the art and herein and refer either to a pluripotent, or lineage-uncommitted, progenitor cell, which is potentially capable of an unlimited number of mitotic divisions to either renew its line or to produce progeny cells which will differentiate into a desired cell type; or a lineage-committed progenitor cell and its progeny, which is capable of self-renewal and is capable of differentiating into a further lineage defined cell type. Unlike pluripotent stem cells, lineage-committed progenitor cells are generally considered to be incapable of giving rise to numerous cell types that phenotypically differ from each other. Instead, they give rise to one or possibly two lineage-committed cell types. As a further description, stem cells are cells capable of differentiation into other cell types, including those having a particular, specialized function (e.g., tissue specific cells, parenchymal cells and progenitors thereof). Progenitor cells (i.e., "multipotent") are cells that can give rise to different terminally differentiated cell types, and cells that are capable of giving rise to various progenitor cells. Cells that give rise to some or many, but not all, of the cell types of an organism are often termed "pluripotent" stem cells, which are able to differentiate into any cell type in the body of a mature organism, although without reprogramming they are unable to de-differentiate into the cells from which they were derived. As will be appreciated, "multipotent" stem/progenitor cells have a more narrow differentiation potential than do pluripotent stem cells. Another class of cells even more primitive (i.e., uncommitted to a particular differentiation fate) than pluripotent stem cells are the so-called "totipotent" stem cells (e.g., fertilized oocytes, cells of embryos at the two and four cell stages of development), which have the ability to differentiate into any type of cell of the particular species. For example, a single totipotent stem cell could give rise to a complete animal, as well as to any of the myriad of cell types found in the particular species (e.g., humans).

Embryonic stem cells are generated and maintained using methods well known to the skilled artisan such as those described by Doetschman et al. (1985) J. Embryol. Exp. Mol. Biol. 87:27-45). Any line of ES cells can be used. One mouse strain that is typically used for production of ES cells, is the 129J strain. Another ES cell line is murine cell line D3 (American Type Culture Collection, catalog no. CKL 1934). Still another ES cell line is the WW6 cell line (Ioffe et al. (1995) PNAS 92:7357-7361). Human embryonic stem cells (hESCs) can be isolated, for example, from human blastocysts obtained from human in vivo preimplantation embryos, in vitro fertilized embryos, or one-cell human embryos expanded to the blastocyst stage (Bongso, et al. (1989), Hum. Reprod., vol. 4: 706). Human embryos can be cultured to the blastocyst stage in G1.2 and G2.2 medium (Gardner, et al. (1998), Fertil. Steril., vol. 69:84). The zona pellucida is removed from blastocysts by brief exposure to pronase (Sigma). The inner cell masses can be isolated by immunosurgery or by mechanical separation, and are plated on mouse embryonic feeder layers, or in the defined culture system as described herein. After nine to fifteen days, inner cell mass-derived outgrowths are dissociated into clumps either by exposure to calcium and magnesium-free phosphate-buffered saline (PBS) with 1 mM EDTA, by exposure to dispase, collagenase, or trypsin, or by mechanical dissociation with a micropipette. The dissociated cells are then replated as before in fresh medium and observed for colony formation. Colonies demonstrating undifferentiated morphology are individually selected by micropipette, mechanically dissociated into clumps, and replated. Embryonic stem cell-like morphology is characterized as compact colonies with apparently high nucleus to cytoplasm ratio and prominent nucleoli. Resulting embryonic stem cells are then routinely split every 1-2 weeks by brief trypsinization, exposure to Dulbecco's PBS (without calcium or magnesium and with 2 mM EDTA), exposure to type IV collagenase (about 200 U/mL), or by selection of individual colonies by mechanical dissociation, for example, using a micropipette.

Once isolated, the stem cells, can be cultured in a culture medium according to the invention that supports the substantially undifferentiated growth of stem cells using any suitable cell culturing technique. For example, a matrix laid down prior to lysis of primate feeder cells (preferably allogeneic feeder cells) or a synthetic or purified matrix can be prepared using standard methods. The stem cells to be cultured are then added atop the matrix along with the culture medium. In other embodiments, once isolated, undifferentiated stem cells can be directly added to an extracellular matrix that contains laminin or a growth-arrested human feeder cell layer (e.g., a human foreskin fibroblast cell layer) and maintained in a serum-free growth environment according to the culture methods of invention. In yet another embodiment, the stem cells can be directly added to a biocompatible cell culture plate in the absence of an extracellular matrix material (e.g., directly on polystrene, glass or the like). Unlike existing embryonic stem cell lines cultured using conventional techniques, embryonic stem cells and their derivatives prepared and cultured in accordance with the methods of the invention avoid or have reduced exposure to xenogeneic antigens that may be present in feeder layers. This is due in part to the media compositions promoting growth in the absence of feeder layers or directly on a cell culture substrate. This avoids the risks of contaminating human cells, for example, with non-human animal cells, transmitting pathogens from non-human animal cells to human cells, forming heterogeneous fusion cells, and exposing human cells to toxic xenogeneic factors.

In yet another aspect, mesenchymal stem cells are used. Mesenchymal stem cells are multipotent stem cells. Mesenchyme is embryonic connective tissue that is derived from the mesoderm and that differentiates into hematopoietic and connective tissue. MSCs can be obtained from both marrow and non-marrow tissues, such as adult muscle side-population cells or the Wharton's jelly present in the umbilical cord.

Substantially homogenous populations of cells (e.g., 80, 90, 95, 98, 99 or 100% homogenous) can be used in the development of metanephric mesenchyme tissue or ureteric bud and Wolffian duct cells. For example, many epithelial organs such as kidney, lung, and prostate under go branching morphogenesis in the course of development. The kidney is formed by mutual induction between two tissues derived from the intermediate mesoderm, the metanephric mesenchyme (MM), and the ureteric bud, Wolffian duct bud, or ureteric and Wolffian duct bud (UB, WD, UB and WD). The UB, WD, or UB and WD induces the MM to differentiate and form the proximal nephron, while the UB, WD, or UB and WD undergoes dichotomous branching and elongation as it invades the MM, ultimately forming the kidney collecting system.

A number of factors are known to cause differentiation of stem cells or progenitor cells along a directed lineage specific for various tissues. Non-limiting examples of bioactive molecules include activin A, adrenomedullin, aFGF, ALK1, ALK5, ANF, angiogenin, angiopoietin-1, angiopoietin-2, angiopoietin-3, angiopoietin-4, angiostatin, angiotropin, angiotensin-2, AtT20-ECGF, betacellulin, bFGF, B61, bFGF inducing activity, cadherins, CAM-RF, cGMP analogs, ChDI, CLAF, claudins, collagen, collagen receptors $\alpha_1\beta_1$ and $\alpha_2\beta_1$, connexins, Cox-2, ECDGF (endothelial cell-derived growth factor), ECG, ECI, EDM, EGF, EMAP, endoglin, endothelins, endostatin, endothelial cell growth inhibitor, endothelial cell-viability maintaining factor, endothelial differentiation shpingolipid G-protein coupled receptor-1 (EDG1), ephrins, Epo, HGF, TNF-α, TGF-β, PD-ECGF, PDGF, IGF, IL8, growth hormone, fibrin fragment E, FGF-5, fibronectin, fibronectin receptor $\alpha_5\beta_1$, Factor X, HB-EGF, HBNF, HGF, HUAF, heart derived inhibitor of vascular cell proliferation, IFN-gamma, IL1, IGF-2 IFN-gamma, integrin receptors, K-FGF, LIF, leiomyoma-derived growth factor, MCP-1, macrophage-derived growth factor, monocyte-derived growth factor, MD-ECI, MECIF, MMP 2, MMP3, MMP9, urokiase plasminogen activator, neuropilin (NRP1, NRP2), neurothelin, nitric oxide donors, nitric oxide synthases (NOSs), notch, occludins, zona occludins, oncostatin M, PDGF, PDGF-B, PDGF receptors, PDGFR-.beta., PD-ECGF, PAI-2, PD-ECGF, PF4, P1GF, PKR1, PKR2, PPARγ, PPARγ ligands, phosphodiesterase, prolactin, prostacyclin, protein S, smooth muscle cell-derived growth factor, smooth muscle cell-derived migration factor, sphingosine-1-phosphate-1 (S1P1), Syk, SLP76, tachykinins, TGF-beta, Tie 1, Tie2, TGF-β, and TGF-β receptors, TIMPs, TNF-alpha, TNF-beta, transferrin, thrombospondin, urokinase, VEGF-A, VEGF-B, VEGF-C, VEGF-D, VEGF-E, VEGF, $VEGF_{164}$, VEGI, EG-VEGF, VEGF receptors, PF4, 16 kDa fragment of prolactin, prostaglandins E1 and E2, steroids, heparin, 1-butyryl glycerol (monobutyrin), and nicotinic amide.

Soluble factors that have been thought to play a role in morphogenetic capacity include hepatocytes growth factor (HGF) and epidermal growth factor (EGF) receptor ligands, which have been shown to induce branching tubular structures in epithelial cells cultured in collagen gels.

The cells used in the generation of the engineered kidney tissue as described herein can be induced to proliferate and/or differentiate using any number or combination of factor such as those described above. In one aspect, the disclosure provides culturing a stem cell in a culture medium comprising a bioactive molecule to expand the stem cells and/or cause differentiation of the stem cell into a ureteric bud or Wolffian duct cell. Such culture conditions can generate a population of ureteric bud cells that can be used as a component for generation of a functioning kidney tissue. In another aspect, the same stem cell type or a different stem cell type can be culture in a culture medium comprising a bioactive molecule to expand the stem cells and/or cause differentiation of the stem cell into a metanephric mesenchyme. Such culture conditions can generate a population of metanephric mesenchyme cells that can be used as a component for generation of a functioning kidney tissue.

Accordingly, the identification of specific soluble factors (e.g., MM-derived soluble factors) mediating UB, WD, or UB and WD branching morphogenesis and culture conditions are useful for proper in vitro development. Hepatocyte growth factor (HGF) has been shown to induce the formation of branching tubular structures with lumens in three-dimensional cultures of epithelial cell lines derived from adult kidneys (i.e., MDCK and mIMCD cells) (Barros et al., 1995; Cantley et al., 1994; Montesano et al., 1991; Santos et al., 1993).

Another group of soluble factors implicated in branching morphogenesis of epithelial cells are the family of epidermal growth factor (EGF) receptor ligands. EGF receptor ligands are capable of inducing the formation of branching tubular structures with lumens in three-dimensional cultures of mIMCD cells, a kidney cell line derived from adult collecting duct cells (Barros et al., 1995; Sakurai et al., 1997).

Tubulogenesis is a phenotypic transformation of the cells such that condensed aggregates of tubule cells form about a central lumen wherein the lumen is bordered by cells possessing a polarized epithelial phenotype and tight junctional complexes along the lumenal border. Conditioned medium elaborated by MM-derived cell lines, BSN-CM, induced UBs, WDs, or UBs and WDs in three-dimensional culture to form branching tubular structures with clearly distinguishable lumens.

A role for GDNF in UB, WD, or UB and WD (from buds or stem cells) development is demonstrated by the disclosure. GDNF plays a role in branching morphogenesis of the isolated UB, WD, or UB and WD and can be used with stem cells.

Studies in the developing mammalian lung and *Drosophila* trachea indicate that members of the FGF family function in branching morphogenesis of epithelial tissues (Hogan, 1999; Metzger and Krasnow, 1999; Zelzer and Shilo, 2000). Furthermore, null mutations of either fgf7 or fgf10 have also been reported to affect kidney development (Obuchi et al., 2000; Qiao et al., 1999), although in both cases the kidneys appear to be modestly affected. For example, in fgf7-null kidneys, there is a 30% reduction in the number of nephrons, and the kidneys appear to function normally (Qiao et al., 1999). Moreover, since FGF7 is detected in the developing kidney after several iterations of UB, WD, or UB and WD branching has already occurred, it is likely that other factors are necessary for the early steps of the branching program. In the case of FGF 10, the defect appears similar. Nevertheless, by potentiating the effect of an essential branching morphogen produced by the MM, certain FGFs are demonstrated herein to play a role in stem cell, UB, WD, or UB and WD branching morphogenesis.

The disclosure demonstrates that UBs, WDs, or UBs and WDs undergo branching tubulogenesis in the presence of a conditioned medium elaborated by a cell line derived from the MM or isolated from an E11.5 mouse (BSN cells). Soluble factors present in BSN-CM are important for UB, WD, stem cells, or UB and WD morphogenesis. Factors that are secreted by the MM are important for the development of the collecting system in artificial systems as well as in vivo.

The MM-derived cell conditioned medium (BSN-CM), when supplemented with GDNF, also induces the isolated UB, WD, stem cells, or UB and WD (in the absence of MM) to undergo dichotomous branching reminiscent of that seen in the developing kidney. This indicates that the MM-derived cell line, reflecting the MM itself, secretes soluble factors capable of inducing branching morphogenesis of the UB, WD, stem cells, or UB and WD. This isolated cell culture system can serve as a powerful assay system since it directly assesses the effect of soluble factors on cell morphogenesis and tubulogenesis.

The disclosure demonstrates that serial liquid column chromatographic fractionation of BSN-CM contain an active morphogenetic fraction comprising a polypeptide (capable of inducing branching morphogenesis comparable to whole BSN-CM). One such polypeptide is pleiotrophin. Pleiotrophin was originally discovered as a fibroblast proliferative factor (Milner et al, BBRC, 165:1096-1103, 1989) and a neurite outgrowth-promoting factor (Rauvala, EMBO J, 8:2933-41, 1989). Outside the nervous system pleiotrophin is generally detected in those embryonic organs in which mesenchymal-epithelial interactions are thought to play an important role, such as salivary glands, lung, pancreas, and kidney (Mitsiadis et al., Development 121:37-51, 1995; Vanderwinden et al., Anat Ebryol (Berl) 186:387-406, 1992). Although pleiotrophin has been shown to be mitogenic for certain epithelial cells (Li et al., Science 250:1690-4, 1990; Sato et al., Exp Cell Res 246:152-64, 1999), there has been no compelling pleiotrophin during epithelial organogenesis.

Immunoblot analysis of BSN-CM as well as in situ hybridization data of developing kidney (Vanderwinden et al., 1992), demonstrate that the embryonic MM is a source of pleiotrophin. In addition to its ability to induce branching morphogenesis in the isolated stem cell, UB, WD, or a combination thereof, pleiotrophin also induced branching tubular structures with lumens, and is thus a soluble factor with this capability. The disclosure provides methods and compositions for use in vitro and in vivo to induce morphogenesis and tubular formation of tissues (e.g., kidney tissue).

The disclosure provides culture techniques and factors, and combination of factors capable of inducing stem cell, UB, WD, or any combination thereof (e.g., UB and WD) to undergo branching morphogenetic activity. In one aspect, the disclosure provides an 18 kDa heparin binding protein, pleiotrophin, obtained from the BSN-CM.

The disclosure demonstrates that pleiotrophin can induce branching morphogenesis of the isolated stem cell, UB, WD, or any combination thereof (e.g., UB and WD) in vitro. Thus, pleiotrophin and compositions comprising pleiotrophin can be used to induce morphogenesis of cells to develop into kidney cells in vitro and in vivo.

A wide range of concentrations of pleiotrophin has been reported to exhibit biological activity (up to 50 µg/ml) in various systems (Imai et al., 1998; Li et al., 1990; Rauvala et al., 1994; Souttou et al., 1997). Pleiotrophin binds to the extracellular matrix, which may explain why concentrations of 200-600 ng/ml were useful for morphogenetic activity in the systems employed in Examples below. In the examples below the stem cell, UB, WD, or any combination thereof (e.g., UB and WD) cell-line and isolated UBs, WDs, or UBs and WDs were cultured in collagen IV or within basement membrane Matrigel™, which could conceivably bind a large fraction of pleiotrophin. In one aspect of the disclosure, similar artificial matrix systems, e.g., cell-free extracellular matrices (e.g., obtained by decellularizing a desired tissue), or synthesized matrices (e.g., lactic acid, glycolic acid, or combinations thereof) can be used and may similarly be modified to bind pleiotrophin.

To date, several glycoproteins, including brain-specific proteoglycans, the receptor type tyrosine phosphatase beta (Maeda and Noda, 1998; Meng et al., 2000) and syndecan-3 (Raulo et al., 1994) have been postulated to function as receptors for pleiotrophin. The UB, WD, or any combination thereof (e.g., UB and WD) has been shown to express syndecan-1 (Vainio et al., 1989), and pleiotrophin is capable of binding to syndecan-1 (Mitsiadis et al., 1995).

The involvement of proteoglycans in pleiotrophin-mediated branching morphogenesis of stem cells, UBs, WDs, or any combination thereof (e.g., UBs and WDs) is particularly interesting in light of data demonstrating the importance of proteoglycans in UB and WD development (Bullock et al., 1998; Davies et al., 1995; Kispert et al., 1996). In these studies, chemical or genetic depletion of sulfated proteoglycans inhibits branching morphogenesis, and this is accompanied by decreased GDNF expression, and loss of c-ret at the UB, WD, or UB and WD tips (Bullock et al., 1998; Kispert et al., 1996). Even at early time points, when c-ret expression is still preserved, addition of exogenous GDNF alone does not completely restore UB, WD, or UB and WD branching morphogenesis (Sainio et al., 1997). One possibility is that depletion of sulfated proteoglycans also affects pleiotrophin-mediated signaling or binding. Accordingly, the disclosure provides that pleiotrophin functions as a MM-derived morphogen acting upon the stem cell, UB, WD, or any combination thereof (e.g., UB and WD). Moreover, the results support the idea that stem cell, UB, WD, or any combination thereof (e.g., UB and WD) branching morphogenesis can be induced by more than a single factor. At least two soluble factors, GDNF and pleiotrophin can be used to induce morphogenetic changes. Other heparin-binding agents including heregulin can also be used in the methods of the disclosure as a substitute for pleiotrophin, for example. GDNF can initiate the stem cell, UB, WD, or any combination thereof (e.g., UB and WD) outgrowth, and pleiotrophin (or other heparin binding agent such as heregulin) can induce proliferation and/or facilitate branching (see Table 2). In addition, the disclosure provides a combination of factors such as pleiotrophin and GDNF and may include FGF. FGF and related members play a facilitory role, since FGF1 potentiates the effects of pleiotrophin on stem cells, UB, WD, or any combination thereof (e.g., UB and WD) on branching morphogenesis, though by itself (with GDNF present) exerts little if any morphogenetic activity.

Inhibitory factors can also play a role in morphogenesis regulation and can include members of the transforming growth factor-beta family (Sakurai and Nigam, 1997). For example, gradients of positive and negative factors, most of which are matrix-bound, may exist in the mesenchyme and stroma. By regulating proliferation, apoptosis and the expression of morphogenetic molecules at branch tips, branch points and stalks, the global and local balance of these stimulatory and inhibitory factors provide determinants of branching patterns during collecting system development. In addition, sulfated proteoglycans should also be present either to maintain expression of these soluble factors or to secure their binding sites. At later stages, other soluble factors such as HGF and/or EGF receptor ligands may play supplementary roles, either during branching (particularly in the later stages) or shaping/maturation of tubular structures.

It should also be noted that the concentration-dependent morphogenetic changes induced by pleiotrophin in the stem cell, UB, WD, or any combination thereof (e.g., UB and WD), provides evidence that pleiotrophin represents a "classical morphogen," in the sense of activin in early *Xenopus* development (Green and Smith, 1990). Such a molecule is expected to produce different phenotypic changes in the responding tissue depending upon the concentration of the molecule to which it is exposed. In this regard, the basement membrane of the developing stem cell, UB, WD, or any combination thereof (e.g., UB and WD) to which pleiotrophin is localized, can act as a "reservoir." Release of pleiotrophin from the basement membrane at the UB, WD, or UB and WD tips, perhaps through digestion by matrix degrading proteases, can produce a local concentration gradient, resulting in increased growth and proliferation of tips, while lower amounts of pleiotrophin along the length of the stalk would induce elongation of the forming tubule. Such a concentration gradient of pleiotrophin provides a basis for modulating the shape and directionality of the developing stem cell, UB, WD, or any combination thereof (e.g., UB and WD).

Populations of UB, WD or UB and WD cells developed by the methods and compositions of the disclosure can be culture in biocompatible matrices or gels used in tissue engineering. Similarly, metanephric mesenchyme cells can be cultured in biocompatible matrices or gels. Furthermore, co-culture of MM and UB, WD or UB and WD cells can be performed in biocompatible matrices or gels. The biocompatible matrix or gel may be designed to promote branching (e.g., by photolithography techniques, printing techniques and the like; see, e.g., Nelson et al., Science 314, 298 (2006), incorporated herein by reference)

Branching Morphogenesis in Organotypic Cultures

Alternatively, the stem cells or UB, WD, or MM progenitor cells of the disclosure may be seeded onto or into a three-dimensional framework or scaffold alone (e.g., as a homogenous population) or in combination (e.g., a heterogeneous population) and cultured to, allow the cells to grow and fill the matrix or immediately implanted in vivo, where the seeded cells will proliferate. Such a framework can be implanted in combination with any one or more growth factors, drugs, additional cell types, or other components that stimulate tissue (e.g., kidney tissue) formation or otherwise enhance or improve the practice of the disclosure.

The cell compositions of the disclosure can be used to produce new kidney tissue in vitro, which can then be implanted, transplanted or otherwise inserted to replace or augment a subject's tissue wherein the kidney tissue becomes vascularized. In a non-limiting embodiment, the stem cells of the disclosure are used to produce a three-dimensional kidney tissue construct in vitro by combining the UB, WD or UB and WD cells with MM cells derived from the stem cells, which are then implanted in vivo.

A biocompatible matrix or gel may be of any material and/or shape that allows cells to attach to it (or can be modified to allow cells to attach to it) and allows cells to grow in more than one layer. A number of different materials may be used to form the matrix, including but not limited to: nylon (polyamides), dacron (polyesters), polystyrene, polypropylene, polyacrylates, polyvinyl compounds (e.g., polyvinylchloride), polycarbonate (PVC), polytetrafluorethylene (PTFE, teflon), thermanox (TPX), nitrocellulose, cotton, polyglycolic acid (PGA), collagen (in the form of sponges, braids, or woven threads, and the like), cat gut sutures, cellulose, gelatin, or other naturally occurring biodegradable materials or synthetic materials, including, for example, a variety of polyhydroxyalkanoates. Any of these materials may be woven into a mesh, for example, to form the three-dimensional framework or scaffold. The pores or spaces in the matrix can be adjusted by one of skill in the art to allow or prevent migration of cells into or through the matrix material.

The three-dimensional framework, matrix, hydrogel, and the like, can be molded into a form suitable for the tissue to be replaced or repaired. For example, various techniques are known wherein a biocompatible matrix can be molded to form tubes, channels, islands, wells, and various shapes.

The stem cells, their progeny, and generated tissue of the disclosure can be used in a variety of applications. These include, but are not limited to, transplantation or implantation of the cells either in unattached form or as attached, for example, to a three-dimensional framework or gel, as described herein.

The cells or tissue developed according to the disclosure can be administered prior to, concurrently with, or following injection of the angiogenic factor. In addition, the cells of the invention may be administered immediately adjacent to, at the same site, or remotely from the site of administration of the angiogenic factor. By angiogenic factor is meant a growth factor, protein or agent that promotes or induces angiogenesis in a subject.

In another aspect of the disclosure, artificial matrices comprising biocompatible material may be used as a support for cell growth. Such matrices may be designed such that concentrations of pleiotrophin may change at desired branch points within the matrix material. In this manner, kidney cells may grow and proliferate through the matrix and branch at locations where pleiotrophin concentrations are at a level to induce branching morphogenesis.

In another embodiment, the disclosure provides clonal subcolonies of specifically engineered, functional kidneys that are suitable for use in screening of drugs and agents to measure effects on specific kidney functions as well as for use in transplantation. Using the compositions and methods of the disclosure, it is possible to culture kidney components derived from a single stem cell, UB, WD, or any combination thereof (e.g. UB and WD) in order to develop a kidney tissue in vitro. Normal kidney development comprises reciprocal interaction between the stem cell, UB, WD, or any combination thereof (e.g. UB and WD) and the metanephric mesenchyme (MM) as described herein. The methods of the disclosure provide the ability to reduce the amount of tissue that must be sacrificed from cadaver tissue or through invasive biopsy techniques in order to obtain sufficient tissue for in vitro generation of kidney tissue for screening and transplantation. The disclosure provides methods and compositions whereby a single progenitor cell or tissue is capable of generating multiple kidney tissues in vitro.

Using the methods of the disclosure and compositions of the disclosure it is possible to stimulate UB, WD, or UB and WD morphogenesis and MM epithelialization. The methods of and compositions provide for kidney development through co-culturing of MM and stem cells, UBs, WDs, or UBs and WDs in culture systems.

Normal kidney development is initiated when the metanephric mesenchyme (MM) induces an epithelial outgrowth of the Wolffian duct, termed the ureteric bud, Wolffian duct bud, or ureteric and Wolffian duct bud (UB, WD, or UB and WD). The disclosure provides methods of developing an in vitro kidney tissue comprising contacting a stem cell, WD, or UB with factors to induce branching morphogenesis and culturing the cells on a biocompatible matrix comprising collagen IV (e.g., Matrigel™). The cells can then be co-cultured with MM. The MM further induces the UB, WD, or UB and WD to elongate and branch, and through multiple iterations of this branching program, the UB, WD, or UB and WD subsequently develops into the renal collecting system. In turn, the branching stem cells, UB, WD, or UB and WD initiates the reciprocal induction of the MM and stimulates it to epithelialize and to form the tubular nephron. These nephrons then connect with the UB, WD, or UB and WD derived collecting system allowing drainage of fluid (e.g., urine) into the bladder in vivo. This process is repeated through successive iterations to achieve the approximately 1 million nephrons present in the adult human kidney. The disclosure also provides for in vivo vascularization of the artificial kidney tissue. For example, once the in vitro generated tissue is developed, implantation into the kidney of a subject results in vascularization of the tissue.

As described herein, the disclosure demonstrates that isolated stem cells, UBs, WDs, or any combination thereof undergoes branching morphogenesis in vitro when exposed to several growth factors including pleiotrophin (PTN) alone or in combination with other factors including glial cell-derived neurotrophic factor (GDNF), fibroblast growth factor-1 or -7 (FGF1, FGF7) and proteins secreted by a mesenchymally derived cell line or any combination thereof. In addition, the disclosure provides methods for regulating processes that govern stem cell, UB, and WD branching morphogenesis, such as the matrix-binding requirements vis-a-vis integrin expression, the dependence of branching morphogenesis on heparin sulfate proteoglycans, and the roles of positive and negative modulators of branching. Other growth factors present in media conditioned by ureteric bud, Wolffian duct bud, or ureteric and Wolffian duct bud cells that can induce differentiation of isolated mesenchyme cultured in vitro include, for example, leukemia-inhibitory factor (LIF) and FGF2.

Subcultures of each of the components of the kidney—the ureteric bud, Wolffian duct bud, or ureteric and Wolffian duct bud and the mesenchyme allow for "staged" development of an artificial kidney tissue. Using the methods and compositions of the disclosure the isolated UB, WD, or UB and WD and mesenchyme can be recombined in vitro and grown in an autonomous fashion. The resultant kidney is morphologically and architecturally indistinguishable from a "normal" kidney and can be used for transplantation, as a source for the study of kidney function, and as a resource for determining drug-effects upon kidney function. Furthermore, the disclosure provides methods for partitioning/propagating the kidney or the cultured isolated ureteric bud, Wolffian duct bud, or ureteric and Wolffian duct bud into smaller fragments and support the in vitro development of these subfractions through several "generations." The methods of the disclosure further allow for these subfractions to be recombined with fresh mesenchyme to develop additional kidney tissue through the induction of the mesenchyme. Furthermore, these nascent nephrons formed contiguous connections with limbs of the branched UB, WD, or UB and WD. Consequently, the disclosure provides in vitro engineered kidney tissue comprising a population of renal primordia suitable for transplantation and derived from a single progenitor.

The methods provided by the disclosure utilize an in vitro, approach to renal engineering that provides an ability to create colonies of kidney tissue (in some cases comprising genetically engineered cells) suitable for transplantation. In one aspect of the disclosure, a stem cell population, an embryonic ureteric bud, Wolffian duct bud, or ureteric and Wolffian duct bud is obtained or separated from the surrounding metanephric mesenchyme and each component (e.g., the MM and UB, WD, or any combination thereof) is cultured in isolation. The stem cell, UB, WD, or combination thereof and/or the MM can modified in vitro (as described herein) in a tailored fashion to express a specific polynucleotide (e.g., a heterologous polynucleotide) or reduce expression of a specific polynucleotide to obtain a desired function (e.g., to reduce expression of immunogenic proteins). The components are then recombined to allow the morphogenesis and development of kidney tissue in vitro (e.g., to generate an in vitro engineered kidney). The in vitro engineered kidney can then be used in transplantation, to screen for desired biological function, and/or to screen for agents, which modulate kidney function.

For example, stem cell, embryonic UB, WD, or UB and WD are dissected and separated from the surrounding tissue or metanephric mesenchyme (MM). The dissected cells are then used to grow an arborized structure, which can be subdivided into smaller fractions and used to induce additional generations of UBs, WDs, or UBs and WDs that grow and branch in vitro. The continued growth and branching is maintained in the culture by culturing and subculturing the stem cells, UBs, WDs, or UBs and WDs in the presence MMs in a culture medium comprising pleiotrophin (e.g. PTN and GDNF or PGN, GNDF and an FGF). The subfraction of UBs, WDs, or UBs and WDs can then be used through multiple generations to renew kidney tissue development. For example, UB, WD, or UB and WD generations can be dissected and recombined with freshly isolated metanephric mesenchyme. The cells retained the ability to induce dramatic tubular epithelial differentiation of the mesenchyme. Furthermore, there appeared to be connections between induced tubules of the mesenchyme and terminal portions of the UB, WD, or UB and WD thereby providing a conduit between the tubule and urinary collecting system. The generated kidney opens up the possibility of uniquely tailoring specific components of either the nephron (derived from the mesenchyme) or tie collecting system (derived from the UB, WD, or UB and WD) in vitro in a potentially functional and transplantable organ.

The source of cells used to ultimately engineer kidney tissues need not be derived from the kidney per se (see, e.g., Kim and Dressler, J Am Soc Nephrol 16: 3527-3534, 2005; incorporated herein by reference). Pluripotent embryonic stem (ES) cells and pluripotent embryonic germ (EG) cells can serve as progenitor cells for a variety of differentiated cell types and recent work with human ES and EG cells has opened the doors to some potential beneficial therapeutics. When cultivated in vitro, human ES and EG cells form 3-dimensional aggregates called embryoid bodies (EB) that can then differentiate into derivatives of all three primary germ cell layers. Furthermore, these EB can be induced to differentiate into specific but different cellular components such as UBs, WDs, or UBs and WD based on conditioning by certain growth factors, such as FGF and TGF-beta. Cells derived from ES and EG cells can organize and can display a diverse set of functional properties. Finally, multipotent adult bone marrow-derived mesenchymal stem cells (MSC) may serve as an adult source of stem cells readily available for engineering of tissues derived from mesenchyme. Within the context of the kidney, cells derived from the bone marrow were found to repopulate or regenerate a variety of renal territories, including the glomerular podocyte and mesangium, interstitium, and renal epithelial tubule. Recent work suggests that there may exist one or more self-renewing "renal stem cells" found within the MM that can differentiate into the myofibroblasts of the renal stroma and/or endothelium. In addition, renal tubular progenitor cells can be obtained using the techniques as described by Maeshima et al., J Am Soc Nephrol 17: 188-198, 2006 (incorporated herein by reference).

As discussed herein, the disclosure provide methods and compositions whereby isolated UBs, WDs, or UBs and WDs can be co-cultured and stimulated by extrinsic factors to induce branching and kidney development. For example, whole isolated intact UB, WD, or UB and WD (cleanly separated from surrounding MM) can be induced to undergo branching morphogenesis in vitro in a manner similar to UB, WD, or UB and WD culture. Suspension of the isolated UBs, WDs, or UBs and WDs within, or on, a natural or artificial biocompatible substrate (e.g., Matrigel™/collagen gel) and when exposed to a mixture of mesenchyme-cultured media augmented with GDNF, results in the isolated unbranched UB, WD, or UB and WD rapidly forming a polarized, extensively branched structure with an internal lumen. As described further herein, pleiotrophin, which induced branching of stem cells, UB, WD, or any combination thereof, also induces branching morphogenesis of the whole ureteric bud, Wolffian duct bud, or ureteric and Wolffian duct bud. This modulation is typically branch-promoting, elongation promoting, or branch-inhibiting. For example, FGF1 induced the formation of elongated stem cells, UB, WD, or any combination thereof branching stalks whereas FGF7 induced amorphous buds displaying nonselective proliferation with little distinction between stalks and ampullae. TGF-beta, which inhibits branching in several cell-culture model systems, also appears to inhibit the branching of the isolated stem cells, UB, WD, or any combination thereof. Endostatin, which is a cleavage product of collagen XVIII normally found in the UB, WD, or UB and WD basement membrane, also selectively inhibits branching of the UB, WD, or UB and WD. Growth factors, such as LIF, have been isolated from UB, WD, or UB and WD conditioned media and induce mesenchymal-to-epithelial transformation of cultured mesenchyme. Other factors, such as FGF2, appear to promote survival but not differentiation of mesenchyme.

The branching isolated ureteric bud, Wolffian duct bud, or ureteric and Wolffian duct bud retains the ability to induce freshly isolated mesenchyme when recombined in vitro without exogenous growth factors. By removing the surrounding biocompatible matrix from the cultured UB, WD, or UB and WD and placing mesenchyme in close proximity, the UB, WD, or UB and WD continues to grow and extend branches into the surrounding mesenchyme. Furthermore, the mesenchyme condenses in areas where the UB, WD, or UB and WD has extended branches, and then epithelializes in a manner similar to normal kidney development. This has wide-ranging implications for in vitro kidney engineering, including the ability to independently culture ureteric bud, Wolffian duct bud, or ureteric and Wolffian duct bud and metanephric mesenchyme, modify their phenotypes in vitro, and then recombine them. For example, it may be possible to develop engineer kidneys with properties such as enhanced drug or toxin secretion by in vitro modification of organic anion transporters, improved immune tolerance by suppression of costimulatory molecules, as discussed herein. The disclosure demonstrates that these recombined "in vitro engineered kidneys," comprised of cultured isolated UB, WD, or UB and WD and freshly isolated mesenchyme, form cohesive intact tubular conduits. That is, the nascent tubular nephron, derived from MM, has a tubular lumen in direct connection with the tubular lumen of the collecting system, derived from the UB, WD, or UB and WD.

The culture system and methods of the disclosure provide the ability to propagate the isolated UB, WD, or UB and WD in vitro through several generations. For example, isolated stem cells, UB, WD, or any combination thereof are cultured in vitro and induced to undergo branching morphogenesis in the presence of BSN-CM or pleiotrophin and GDNF or pleiotrophin, FGF1, and GDNF. After 8 days, the cultured bud is subdivided into approximate 3rds and resuspended within a suitable biocompatible matrix (Matrigel™/collagen gel). This 2nd generation bud is further subdivided after another 8 days of culture, and the 3rd generation bud is cultured for 8 days (thus yielding at least 9 subdivided buds from one progenitor bud). These subsequent clonal generations of cultured UB, WD, or UB and WD retain the ability of the progenitor bud to induce mesenchyme upon in vitro recombination. The buds also retained the capacity to form cohesive conduits with the mesenchymally-derived tubules that they induced. Thus, the disclosure provides the ability to develop and propagate a clonal, expanded, and long-lived colony of ureteric bud, Wolffian duct bud, or ureteric and Wolffian duct buds, derived from a single progenitor bud that retains the properties of the progenitor. Using similar techniques with the MM, it is possible to develop colonies of mesenchyme derived from a single progenitor mesenchyme that can then be recombined with a propagated UB, WD, or UB and WD.

Whole embryonic kidneys can be propagated in a similar manner in vitro. After culturing these kidneys for 3 days, it is possible, using the methods of the disclosure, to subdivide into approximate 3rds the whole cultured kidney and then propagate the subsequent generations in vitro. At least 3 generations, yielding 9 kidneys, were generated from a single progenitor kidney using the methods and compositions of the disclosure. Thus, the methods and compositions of the disclosure provide the ability for expansion of syngenic rudiments in vitro prior to transplantation into suitable hosts.

In many tissue-engineering technologies, an extrinsic biocompatible scaffold is required to provide orientation and support to the developing tissue. In one sense, the native polymeric basement membrane (BM) is a bioactive scaffold directing the normal development of the kidney. BM constituents such as endostatin can directly influence branching of the UB, WD, or UB and WD, and other components, such as HSPGs, can indirectly regulate growth by binding and releasing growth factors. The bioartificial scaffolds used in tissue engineering can be synthetic or biologic and contain or can be coated with ECM constituents, such as collagen or proteoglycans. Exciting new techniques in materials science are emerging that allow these scaffolds to be impregnated with drugs, proteins, or even DNA, and thus may be more biologically relevant. By combining a truly bioactive scaffold with cultured pluripotent cells, such as ES cells, or multipotent cells, such as MSCs or other progenitor cells derived from the mesenchyme, it may be possible to coordinate inductive signals required to derive/engineer an organ such as the kidney. For example, by varying the concentration of factors at points where branching is desired, it is possible to design a tissue having a predicted number of branch point.

Biocompatible support materials (biocompatible scaffolds) for culturing kidney cells include any material and/or shape that: (a) allows cells to attach to it (or can be modified to allow cells to attach to it); and (b) allows cells to grow in more than one layer. A number of different materials may be used as a culture support, including, but not limited to, nylon (polyamides), dacron (polyesters), polystyrene, polypropylene, polyacrylates, polyvinyl compounds (e.g., polyvinylchloride), polycarbonate (PVC), polytetrafluorethylene (PTFE; teflon), thermanox (TPX), nitrocellulose, cotton, polyglycolic acid (PGA), cat gut sutures, cellulose, gelatin, dextran, collagen, decellulularized tissue (both allogenic and xenogeneic), and like.

In one aspect of the disclosure a ureteric bud, Wolffian duct bud, or ureteric and Wolffian duct bud is used as a bioactive scaffold, which could then serve as a biologically-relevant orchestrator (conductor) of the complex inductive signals that underlie "normal" renal development. In an organ such as the kidney, where development is dependent on coordinated interactions between epithelium and mesenchyme, utilization of a biologically active epithelial scaffold to induce proper differentiation, maturation and integration of surrounding multipotent cells may provide a unique opportunity to modify specific cellular functions in vitro but yet to retain the complex organizational direction required to develop a mature kidney. This principle is applicable to engineering of other organs, such as lung, liver, pancreas, salivary gland or breast, which are also dependent upon mesenchymal-epithelial interactions within the context of a branching epithelial derivative. In one experiment, the stem cells, UB, WD, or any combination thereof, are co-cultured with lung mesenchyme, can begin to express surfactant protein. Accordingly, the methods and compositions serve as a scaffold for a number of novel "chimeric" organs. The ability to independently culture and then combine mesenchymally-derived elements with epithelial-derived elements allow for the integration of cellular and organ-based approaches to tissue engineering. This approach would allow one to modify cell-based elements in vitro to possess certain desirable properties but still take advantage of an organ-based approach to tissue engineering.

By culturing kidney tissue derived from stem cells, UB, WD, or UB and WD and MM in vitro, the disclosure provides the unique opportunity to modulate each of their component functions in a site-specific manner. For example, transfection of the mesenchyme with constructs expressing organic ion transporters would lead to increased capability to handle drugs and toxins, insertion of genes coding for growth factors, such as insulin-like growth factor (IGF), would lead to markedly enhanced in vitro engineered kidney development and improved functionality, insertion of immunomodulatory elements, such as repressors of co-stimulatory molecules, could be used to improved immune tolerance; stimulation of branching in the UB, WD, or UB and WD can lead to an increased number of resultant nephrons and improved renal functionality. Thus, there are numerous of ways to design an in vitro engineered kidney with tailored function. Furthermore, by subcloning UBs, WDs, or UBs and WDs, the disclosure provides the potential to develop a large number of kidneys derived from a single progenitor, thus removing concerns surrounding limited supply of transplantable tissue. Third, it is possible to create a chimeric kidney using the UB, WD, or UB and WD as a scaffold and recombining the UB, WD, or UB and WD with heterologous mesenchymal cells. These mesenchymal cells could be derived from embryonic stem cells that, when exposed to kidney derived signals from the UB, WD, or UB and WD induce differentiation of the renal mesenchymal cells into epithelial tissues. In normal adults, stem cells originating in the bone marrow repopulate portions of the kidney and differentiate into renal cells, and it is likely that embryonic stem cells also posses this ability.

The approach provided by the methods and compositions of the disclosure, whereby in vitro engineered kidneys developed and/or are designed to possess specific functions, such as improved immune tolerance or enhanced tubular secretion of substrate, offer original approaches to transplantation and kidney therapy. Furthermore, creating clonal populations of in vitro engineered kidneys creates the potential for development of organ propagation from a single tissue. This approach is potentially applicable to other epithelial tissues such as lung and pancreas.

The methods provided by the disclosure allow for the development of colonies of subcloned in vitro engineered kidneys that have been specifically tailored to express certain functions, and are immune-naïve, particularly where the tissue is derived from stem cells. Immune naïve means that the cells lack "self" identification as the cells were fetally or stem cell derived and therefore should be immune tolerant.

Methods of transfecting and transforming cells are known in the art. For example, methods of transfecting/transforming kidney cell are known and include the following methods. Tomita et al. (Biochem. and Biophys. Res. Comm. 186:129-134, 1992) report a method for in vivo gene transfer into the rat kidney. They utilize HVJ (Sendai virus) and liposome methodology. In this protocol, plasmid DNA and a nuclear protein are coencapsulated in liposomes and later cointroduced into cells. The reporter gene utilized in these studies was the SV40 large T antigen. The gene transfer can be performed by inserting a cell or culture of kidney tissue with a liposome suspension. Transfection/transformation of the kidney cells can be assay by detecting SV40 large T antigen immunohistochemically. A study by Zhu et al. (Science 261: 209-11, 1993), reports the use of a particular cationic liposome DNA mixture to deliver genes with high efficiency into a vast number of endothelial cells in a rat. Moullier et al. (Kidney International 45:1220-1225, 1994) provides a first report of an adenoviral-mediated gene transfer into a kidney.

As used herein, the term "transfect" or "transform" refers to the transfer of genetic material (e.g., DNA or RNA) of interest via a vector into cells of a mammalian organ or tissue (e.g., kidney/renal tissue). The vector will typically be designed to infect mammalian kidney cell. The genetic material of interest encodes a product (e.g., a protein polypeptide, peptide or functional RNA) whose production by kidney cells is desired. For example, the genetic material of interest can encode a hormone, receptor, enzyme or (poly)peptide of therapeutic value. Examples of genetic material of interest include but are not limited to DNA encoding cytokines, growth factors and other molecules which function extracellularly such as chimeric toxins, e.g., a growth factor such as interleukin-2 (IL-2) fused to a toxin, e.g., the pseudomonas exotoxin, dominant negative receptors (soluble or transmembrane forms), truncated cell adhesion or cell surface molecules with or without fusions to immunoglobulin domains to increase their half-life (e.g., CTLA4-Ig). For example, cells of an organ or a tissue do not express a gene product encoded by the genetic material prior to transfection or transformation. Alternatively, infection of the cells of an organ or a tissue may result in an increased production of a gene product already expressed by those cells or result in production of a gene product (e.g., an antisense RNA molecule) which decreases production of another, undesirable gene product normally expressed by the cells of that organ or tissue. Generally, the genetic material encodes a gene product, which is the desired gene product to be supplied to the cells of that organ or tissue. Alternatively, the genetic material encodes a gene product, which induces the expression of the desired gene product by the cells of that organ or tissue (e.g., introduced genetic material encodes a transcription factor which induces the transcription of the gene product to be supplied to the subject). Furthermore, the genetic material could simply contain a polynucleotide, e.g., in the form of single stranded DNA to act as an antisense nucleotide. A genetic material infected into a cell of an organ or a tissue via a vector is in a form suitable for expression in the cell of the gene product encoded by that genetic material. Accordingly, the genetic material includes coding and regulatory sequences required for transcription of a gene (or portion thereof) and, when the gene product is a protein or peptide, translation of the gene product encoded by the genetic material. Regulatory sequences which can be included in the genetic material include promoters, enhancers and polyadenylation signals, as well as sequences necessary for transport of an encoded protein or peptide, for example N-terminal signal sequences for transport of proteins or peptides to the surface of the cell or for secretion, or for cell surface expression or secretion preferentially to the luminal or basal side. Enhancers might be ubiquitous or tissue or cell specific or inducible by factors in the local environment, e.g., inflammatory cytokines.

As used herein, the term an "effective amount" refers to a level of expression of a heterologous polynucleotide transfected or transformed into a kidney cell, which brings about at least partially a desired therapeutic or prophylactic effect in an organ or tissue infected by the method of the invention. For example, expression of genetic material of interest can then result in the modification of the cellular activities, e.g., a change in phenotype, in an organ or a tissue that has been infected by the method of the disclosure. In one embodiment, an effective amount of the expression of a heterologous genetic material of interest results in modulation of cellular activity in a significant number of cells of an organ transfected or transformed with the heterologous polynucleotide. A "significant number" refers to the ability of the vector to infect at least about 0.1% to at least about 15% of the renal endothelial cells or UBs, WDs, or UBs and WDs. Typically, at least about 5% to at least about 15% of the cells are transfected/transformed. Most commonly, at least about 10% of the cells are transfected/transformed.

A vector refers to a polynucleotide molecule capable of transporting another nucleic acid to which it has been linked into cells. Examples of vectors that exist in the art include: plasmids, yeast artificial chromosomes (YACs) and viral vectors. However, the invention is intended to include such other forms of vectors which serve equivalent functions and which become known in the art subsequently hereto.

The efficacy of a particular expression vector system and method of introducing genetic material into a cell can be assessed by standard approaches routinely used in the art. For example, DNA introduced into a cell can be detected by a filter hybridization technique (e.g., Southern blotting) and RNA produced by transcription of introduced DNA can be detected, for example, by Northern blotting, RNase protection or reverse transcriptase polymerase chain reaction (RT-PCR). The gene product can be detected by an appropriate assay, for example by immunological detection of a produced protein, such as with a specific antibody, or by a functional assay to detect a functional activity of the gene product, such as an enzymatic assay. If the gene product of interest to be expressed by a cell is not readily assayable, an expression system can first be optimized using a reporter gene linked to the regulatory elements and vector to be used. The reporter gene encodes a gene product, which is easily detectable and, thus, can be used to evaluate the efficacy of the system. Standard reporter genes used in the art include genes encoding β-galactosidase, chloramphenicol acetyl transferase, luciferase and human growth hormone.

The method of the disclosure can be used to infect kidney cells to obtain designer kidneys (e.g., genetically engineered kidney cells). As used herein, the term "kidney cells" is intended to including UB, WD, or UB and WD and MM cell types as well as the other 15 different cell types, e.g., glomerular cells, mesangial cells, interstitial cells, tubular cell, endothelial cells, are intended to be encompassed by the term "kidney cells".

The method of the disclosure can also be used to infect a kidney tissue generated ex vivo. For example, in a transplant setting, a kidney is engineered by the methods of the disclosure, the "in vitro engineered kidney" is then perfused (e.g., the collecting ducts) with a vector carrying genetic material of interest.

One potential application of the disclosure is in renal allograft or xenograft tissue transplantation. In this aspect, kidney tissue generated by the methods and compositions of the disclosure are transfected/transformed with an agent (e.g., delivered to MM cells and/or UBs, WDs, or UBs and WDs) that results in organ tolerance or might help in the postoperative period for decreasing the incidence of early transplant rejection or function (e.g., due to acute tubular necrosis). Either the organ can be made less immunogenic so as to reduce the number of host T cells generated and/or the endothelial cells (e.g., endothelial cells derived from MM) can be altered so as to prevent the adhesion/transmigration of primed immune T-cells or killer effector T-cells (e.g., by use of IL-2-toxin fusion proteins). Moreover, genes transfected/transformed into in vitro engineered kidney tissue, such as nitric oxide synthetase (NOS), prior to transplantation could also serve to protect the organ post transplantation. These strategies make clinical sense since it is well known that early rejection episodes and malfunction lead to a worse long-term graft survival. Therefore, prevention of acute rejection and preservation of function immediately post transplant are of particular importance. Delivery of the genetic material (i.e., the heterologous polynucleotides) for this purpose can be done using methods known in the art including utilizing an adenovirus vector, lipofection, or other techniques known in the art. In addition to the heterologous polynucleotides mentioned above, these vectors can carry additional sequences comprising anti-sense constructs to one or more cell adhesion molecules (involved in lymphocyte homing) or dominant negative constructs to these molecules, or antisense constructs to MHC antigens in the transplant or locally immune suppressive lymphokines such as interleukin-10 (IL-10) or viral IL-10 or chimeric toxins which would preferentially kill T-cells, e.g., IL-2 toxin fusion protein. It is also possible that one could interfere with the recognition part of the immune system by, for example, the local secretion of CTLA4-IgG fusion proteins. This list of candidate polynucleotides is not exhaustive. Those skilled in the art of transplantation know of others. The genes could be delivered with constitutive promoters or with appropriate inducible enhancers.

In another aspect of the disclosure, the kidney cultures (UB, WD, or UB and WD alone, MM alone, and co-cultures thereof) may be used in vitro to screen a wide variety of compounds, such as cytotoxic compounds, growth/regulatory factors, pharmaceutical agents, and the like to identify agents that modify kidney function and/or cause cytotoxicity and/or kidney cell death or modify kidney proliferative activity. Examples of such agents or compounds include growth factors, peptides, and small organic molecules. In another aspect, the cells can be genetically engineered and the kidney culture implanted in vivo, whereby screening can be measured by detecting changes in the kidney culture using a genetically engineered label. In this aspect, vascularization can assist in providing information on the effect an agent has on kidney tissue.

To this end, the cultures (e.g., stem cells, UB, WD, or UB and WD primary cells, UB, WD, or UB and WD cell lines, MM cells, whole organ cultures, MM/spinal cord co-cultures, and UB, WD, OR UB AND WD/MM co-cultures) are maintained in vitro and exposed to the compound to be tested. The activity of a cytotoxic compound can be measured by its ability to damage or kill cells in culture or by its ability to modify the function of kidney cells (e.g., UB, WD, or UB and WD proliferative capacity, branching capacity, MM epithelialization capacity, particular gene expression, cell size, cell morphology, protein expression, and the like). This may readily be assessed by vital staining techniques, ELISA assays, immunohistochemistry, PCR, microarray analysis, and the like. The effect of growth/regulatory factors on the kidney cells (e.g., UBs, WDs, or UBs and WDs, MMs) may be assessed by analyzing the cellular content of the culture, e.g., by total cell counts, and differential cell counts, including the number of branch points. This may be accomplished using standard cytological and/or histological techniques including the use of immunocytochemical techniques employing antibodies that define type-specific cellular antigens. The effect of various drugs on normal cells cultured in the culture system may be assessed. For example, UB, WD, or UB and WD primary cells or cell lines may be cultured in vitro under conditions that stimulate branching morphogenesis/tubulogenesis (e.g., in the presence of BSN-CM, pleiotrophin, or pleiotrophin+other factors). A test compound is then contacted with the culture and the effect the test compound has on branching morphogenesis/tubulogenesis can be compared to a control, wherein a difference is indicative of an compound that increases or decreases branching morphogenesis.

The cytotoxicity to kidney cells (e.g., human UBs, WDs, or UBs and WDs and co-cultures of MM and UBs, WDs, or UBs and WDs) of pharmaceuticals, anti-neoplastic agents, carcinogens, food additives, and other substances may be tested by utilizing the culture system of the invention.

First, a stable, growing kidney culture comprising UB, WD, OR UB AND WD and/or MM cells is established. Then, the culture is exposed to varying concentrations of a test agent. After incubation with a test agent, the culture is examined by phase microscopy to determine the highest tolerated dose—the concentration of test agent at which the earliest morphological abnormalities appear. Cytotoxicity testing can be performed using a variety of supravital dyes to assess cell viability in the culture system, using techniques known to those skilled in the art.

Once a testing range is established, varying concentrations of the test agent can be examined for their effect on viability, growth, and/or morphology of the different cell types constituting the kidney culture by means well known to those skilled in the art.

Similarly, the beneficial effects of drugs may be assessed using the culture system in vitro; for example, growth factors, hormones, drugs which enhance kidney formation, or activity (e.g., branching activity) can be tested. In this case, stable cultures may be exposed to a test agent. After incubation, the cultures may be examined for viability, growth, morphology, cell typing, and the like as an indication of the efficacy of the test substance. Varying concentrations of the drug may be tested to derive a dose-response curve.

The culture systems of the disclosure may be used as model systems for the study of physiologic or pathologic conditions. For example, in a specific embodiment of the invention, the culture system can be optimized to act in a specific functional manner as described herein by modifying genome of the cells.

The kidney culture system of the disclosure may also be used to aid in the diagnosis and treatment of malignancies and diseases. For example, a biopsy of a kidney tissue may be taken from a subject suspected of having a malignancy or other disease or disorder of the kidney. The biopsy cells can then be separated (e.g., UBs, WDs, or UBs and WDs from MM cells etc.) and cultured in the according to the methods of the invention. UBs, WDs, or UBs and WDs from the subject can be co-cultured with normal (e.g., heterologous MM cells) to determine biological function of the UBs, WDs, or UBs and WDs compared to UBs, WDs, or UBs and WDs derived from a normal kidney. Similarly MM cells from the subject can be cultured with normal UBs, WDs, or UBs and WDs to examine MM function and activity. In addition, such cultures obtained from biopsies can be used to screen agent that modify the activity in order to identify a therapeutic regimen to treat the subject. For example, the subject's culture could be used in vitro to screen cytotoxic and/or pharmaceutical compounds in order to identify those that are most efficacious; i.e. those that kill the malignant or diseased cells, yet spare the normal cells. These agents could then be used to therapeutically treat the subject.

Where in vitro engineered kidney tissue is generated according to the methods and compositions of the disclosure transplantation of the tissue can be performed as follows. Surgery is performed on the recipient subject to expose one or both kidneys. The in vitro engineered kidney tissue is implanted directly into/adjacent to the recipient subject's kidney to result in the formation of chimeric kidney, or into a fold of the omentum where it forms a chimeric kidney that functions independently of the recipient's kidney. The omentum, which is a membranous structure that connects the bowels, is a highly vascularized tissue sufficient for the transplantation of the in vitro engineered kidney. The in vitro engineered kidney can be placed adjacent to any portion of the omentum, however, in one aspect the in vitro engineered kidney is transplanted at or near an omental fold. In another aspect, the in vitro engineered kidney is transplanted at an omental fold located near one of the recipient's kidneys, particularly near the ureter, so that the developing ureter of the metanephros can be readily connected to the recipient's excretory system.

When implanted into the recipient's kidney, an incision, large enough to receive the in vitro engineered kidney tissue is made in the fibrous renal capsule that surrounds the recipient's kidney. The location of the incision can be anywhere in a viable portion of the recipient's kidney, but most conveniently will be at an external border of the kidney that is easily accessible during surgery. The in vitro engineered kidney tissue is placed between the capsule and the cortex of the recipient kidney.

The implanted in vitro engineered kidney tissue is allowed to grow within the recipient under conditions that allow the tissue to vascularize. Suitable conditions may include the use of pre or post-operative procedures to prevent rejection of the implant as well as the administration of factors (e.g., pleotrophin, FGF1, GNDF, and the like) that stimulate tubulogenesis and/or morphogenesis of the in vitro engineered kidney tissue. Immunosuppression techniques (in the absence or combined with genetically engineered techniques) such as cyclosporin A (CSA) to prevent rejection of the donor tissue are known in the art.

EXAMPLES

Fibroblast growth factor-1 (FGF1) and glial cell-derived neurotrophic factor (GDNF) were obtained from R&D Systems (Minneapolis, Minn.). Mouse anti-E-cadherin antibodies were from BD Biosciences Pharmingen™ (San Diego, Calif.) and goat anti-mouse AlexaFluor® 594 was from Molecular Probes (Eugene, Oreg.). FITC-conjugated D. biflorus (DB) lectin and rhodamine-conjugated PNA were from Vector Laboratories (Burlingame, Calif.). Type I and type IV collagens, and growth factor-reduced Matrigel™ were from BD Biosciences (San Jose, Calif.). Antibiotics, DMEM:F12 1:1 (v:v) and PBS were from GIBCO-BRL (Grand Island, N.Y.). Unless otherwise noted, all other reagents are from Sigma (St. Louis, Mo.).

Embryos from timed pregnant Holtzman rats (Harlan, Indianapolis, Ind.) at day 13 (E13) of gestation (day 0 being the day of appearance of the vaginal plug) or timed pregnant HoxB7-GFP mice embryos at E12 were dissected free of surrounding tissues. The urogenital tract was isolated and WDs were dissected free of surrounding tissue. The mesonephric tubules and intermediate mesoderm was carefully stripped away leaving only the epithelial tube of the WD. Metanphric kidneys were isolated and directly used in the kidney culture as described below or further separated in to the UB and MM tissues.

Unless otherwise stated, the incubations were performed at 37° C. in an atmosphere of 5% $CO_2$ and 100% humidity. For the immunodetection of pleiotrophin either on western blots or frozen sections of El 3 mouse kidney, a goat anti-pleiotrophin antibody (R&D systems) was used.

Conditioned medium secreted by metanephric mesenchyme-derived cells is required for isolated UB, WD, or UB and WD branching morphogenesis. To identity mesenchymal factors that induce branching morphogenesis of the ureteric bud, Wolffian duct bud, or ureteric and Wolffian duct bud (UB, WD, or UB and WD), a metanephric mesenchyme (MM)-derived cell line (BSN cells) was employed as a substitute for the embryonic MM. These cells were derived from the embryonic day 11.5 (E11.5) MM from a SV40 large T-expressing transgenic mouse and have been extensively characterized. BSN cells are positive for vimentin and negative for cytokeratin, E-cadherin, and ZO-1 by immunostaining, as well as negative for *Dolichos biflorus* lectin-binding. By PCR the cells express WT1 and are negative for c-ret. The cells also express mRNA for growth factors such as HGF and TGFβ by northern blot. cDNA array analysis has confirmed their non-epithelial character. Most importantly, conditioned medium elaborated by BSN cells (BSN-CM) acts similar to the MM by inducing branching morphogenesis of cultured UBs, WDs, or UBs and WDs and the isolated UB, WD, or UB and WD (in the presence of GDNF).

UBs, WDs, or UBs and WDs isolated from El3 rat embryos, when suspended in an extracellular matrix gel and cultured in the presence of BSN-CM (with GDNF), grew to form impressive multiply branching tubular structures comparable to those seen in in vivo kidney development (though the growth was non-directional) (FIG. 1B). In the absence of BSN-CM, however, the UBs, WDs, or UBs and WDs failed to develop. Thus, BSN-CM contains an additional soluble factor(s) necessary for epithelial cell branching morphogenesis. Using this isolated UB, WD, or UB and WD culture model as an assay, key morphogenetic factor present in the BSN-CM were identified.

Example 1

BSN cells were grown to confluency in DMEM/F12 supplemented with 10% fetal calf serum (FCS). The growth media was removed and the cells were then incubated in serum-free DMEM/F12 for 3-4 days followed by collection of the conditioned medium. Swiss ST3 cells (ATCC) were grown to confluence in DMEM with 10% FCS. Once the cells were confluent, the growth media was replaced with DMEM supplemented with 2% FCS and the cells were cultured for an additional 3-4 days. The conditioned medium was collected and used for the experiments. UBs, WDs, or UBs and WDs were cultured in DMEM supplemented, with 10% FCS at 32° C. in an atmosphere of 5% $CO_2$ and 100% humidity.

Example 2

Timed pregnant female Sprague-Dawley rats at day 13 of gestation (day 0 coincided with appearance of the vaginal plug) were sacrificed and the uteri were removed. The embryos were dissected free of surrounding tissues and the kidneys were isolated. For the culture of the whole kidney rudiment, 2-3 kidneys were applied directly to the top of a polyester Transwell filter (0.4 µm pore size; Corning-Costar). The Transwells were then placed within individual wells of a 24-well tissue culture dish containing 400 µl DMEM/F12 supplemented with 10% FCS with or without purified pleiotrophin. Following 7 days of culture, the kidneys were fixed in 2% paraformaldehyde and doublestained with fluorescein-conjugated *Dolichos biflorus*, a lectin which binds specifically to UB, WD, or UB and WD-derived structures, and rhodamine conjugated peanut agglutinin, a lectin which binds to structures derived from the MM. Fluorescent staining was detected using a laser-scanning confocal microscope (Zeiss).

In the case of culture of the isolated UB, WD, or UB and WD, the isolated kidneys were trypsinized for 15 min at 37° C. in L-15 media containing 2 µg/ml trypsin (Sigma). Trypsin digestion was arrested by the addition of 10% FCS and the kidneys were removed to fresh L-15 where the UBs, WDs, or UBs and WDs were isolated from surrounding MM by mechanical dissection. isolated UBs, WDs, or UBs and WDs were suspended within an extracellular matrix gel [1:1 mixture of growth factor reduced Matrigel™ (BD) and Type 1 collagen (BD)] applied to the top of a polyester Transwell filter (0.4 µm pore size; Corning-Costar). The Transwells were placed within individual wells of a 24-well tissue culture dish containing 400 µl of either whole BSN-CM, purified tractions of BSN-CM, or D-12 which were supplemented with human recombinant FGF1 (250 ng/ml; R&D Systems), rat recombinant GDNF (125 ng/ml; R&D Systems) and 10% FCS and cultured. Phase-contrast photomicrographs of the developing UB, WD, or UB and WD were taken using a RT-Slider Spot Digital Camera (Diagnostic Instruments Inc.) attached to a Nikon Eclipse TE300 Inverted Microscope.

Example 3

Confluent monolayers of UBs, WDs, or UBs and WDs were removed from tissue culture dishes by light trypsinization and the cells. 20,000 cells/ml were suspended in an extracellular matrix gel composed of 80% Type 1 collagen and 20% growth factor-reduced Matrigel™. 100 µl of the UB, WD, or UB and WD cell-containing gel was then aliquoted into individual wells of a 96-well tissue culture plate. After gelation, 100 µl of growth medium (DMEM/F12 with or without purified pleiotrophin) supplemented with 1% FCS was applied to each well and the cultures were incubated at 32° C. in 5% $CO_2$ and 100% humidity. Following 4 days of culture, the percentage of cells/colonies with processes was counted as an indicator of the tubulogenic activity. Phase-contrast photomicrographs were taken as described herein.

Example 4

1.5-2 L of BSN-CM collected as described herein was filtered to remove extraneous cellular debris using a 0.22 µm polyethersulphone membrane filter (Corning). The BSN-CM was then concentrated 40-fold using a Vivatlow™ 200 concentrator with a 5 kDa molecular weight cutoff (Sartorius). After adjusting the salt concentration to 0.4 M NaCl, the concentrated BSN-CM was then subjected to sequential liquid column chromatography using an AKTA purifier (Amersham-Pharmacia). Initial fractionation was performed using a heparin sepharose chromatography column (HiTrap™ heparin, 5 ml; Amersham Pharmacia). The flow-through fraction was collected and individual 5 ml fractions of the heparin-bound proteins were eluted via increasing concentrations of NaCl (0.4 M-2.0M) buffered to pH 7.2 with 50 mM HEPES. Aliquots of each fraction were subjected to buffer exchange by dia-filtration using an Ultrafree™ 500 spin column (Millipore) according to the manufacturer's instructions and then tested for morphogenetic activity using the isolated UB, WD, OR UB AND WD culture system.

An active fraction corresponding to the 1.2-1.4 M NaCl eluate was identified based on its ability to induce branching morphogenesis of the isolated UB, WD, or UB and WD. After adjusting this fraction to 1.7 M ammonium sulfate (pH 7.2) it was subjected to further fractionation using a Resource phenyl sepharose hydrophobic interaction column (1 ml; Amersham-Pharmacia). The flow through was collected and 1 ml fractions of bound proteins were eluted with decreasing concentrations of ammonium sulfate (1.7 M-0 M). After buffer exchange, the individual fractions were again tested for their ability to induce UB, WD, or UB and WD branching morphogenesis.

The morphogenetically active fractions from the hydrophobic interaction column were diluted 10-fold with 50 mM HEPES and applied to a Resource S cation exchange column (1 ml; Amersham-Pharmacia). The flow-through was collected and individual 1 ml fractions of bound proteins were eluted—using increasing NaCl concentrations (0 M-2.0 M) and assayed for the ability to induce branching morphogenesis.

The active fractions from the Resource S cation exchange column were subjected to further fractionation using a Superdex™ 200 gel filtration column (Amersham-Pharmacia). Individual 1 ml fractions were collected and assayed for morphogenetic activity. In addition, the active fractions from the Resource S cation exchange column were subjected to SDS-PAGE and the proteins were visualized using coumassie blue (Colloidal Coumassie; Invitrogen) staining. Individual protein bands were cut out of the gels and submitted for microsequencing. Sequence analysis of the protein bands was performed at the Harvard Microchemistry Facility by microcapillary reverse phase HPLC nanoelectrospray tandem mass spectrometry (pLC/MS/MS) on a Finnigan LCQ DECAT™ quadrupole ion trap mass spectrometer.

SDS-PAGE and silver staining of BSN-CM revealed the presence of many protein bands. As described above, liquid column chromatography was used to fractionate BSN—CN and each fraction was tested for its ability to induce branching morphogenesis of the isolated UB, WD, or UB and WD. Of the multiple columns tested, a heparin sepharose column was found to adsorb most of the morphogenetic activity. Within this heparin-binding fraction, the fraction, which eluted at a NaCl concentration of 1.2-1.4 M possessed particularly strong morphogenetic activity. Silver stain analysis of this fraction revealed the presence of prominent lower molecular weight (40 kDa) protein bands. This active fraction was then applied to a Resource phenyl sepharose hydrophobic interaction column. A morphogenetic activity was eluted from this column at 1.4 1.2 M ammonium sulfate. Again, silver staining of this peak fraction revealed prominent low molecular weight protein bands. This active fraction was diluted 10-fold with 50 mM HEPES (pH 7.2) buffer and applied to a Resource S cation exchange column. Each 1 ml fraction of the Resource S eluate was substituted for whole BSN-CM in the isolated UB, WD, or UB and WD culture and compared with BSN-CM itself. Of the 8 fractions eluted from the column, Fraction 4, the peak protein fraction, induced significant UB, WD, or UB and WD morphogenesis. SDS-PAGE analysis and silver staining of this peak fraction revealed the presence of a single protein band with an approximate molecular weight of 18 kDa. This protein band was subjected to in-gel digestion followed by tandem mass spectrometry and was identified as pleiotrophin. (This type of experiment was performed at least 3 times during different purifications, and pleiotrophin was always detected by mass spectrometry).

The presence of pleiotrophin in the active fraction (fraction 4) was confirmed by immunoblot analysis using anti-pleiotrophin antibodies. The morphogenetic activity of individual fractions corresponded to the presence of pleiotrophin in that fraction. In a similar fashion, further purification of the peak fraction from Resource S column was accomplished by applying the active fraction to a Superdex™ 200 gel filtration column. A single protein peak eluted at 15.93 ml, corresponding to a protein with a molecular weight of approximately 18 kDa, and was positive for pleiotrophin by immunoblot. This fraction induced isolated UB, WD, or UB and WD branching morphogenesis. Taken together, these results identify pleiotrophin as a morphogenetic factor present in BSN-CM.

Previous studies have found that pleiotrophin can be isolated to homogeneity from a conditioned medium elaborated by Swiss 3T3 cells. Thus, using this alternative purification procedure, a pure fraction of pleiotrophin was isolated from 3T3 conditioned medium (3T3-CM), as confirmed by silver stain, immunoblot analysis and mass spectrometry. Like the pleiotrophin that purified from BSN cells, this pure pleiotrophin was capable of inducing impressive branching morphogenesis of the isolated UB, WD, or UB and WD. Thus, pleiotrophin purified from two different cell lines gave the same results.

Nevertheless, to provide further confirmation that pleiotrophin is the factor inducing the morphogenetic changes observed in the isolated UB, WD, or UB and WD culture the ability of polyA-sepharose to adsorb pleiotrophin. Treatment of purified pleiotrophin with polyA-sepharose beads results in the loss of detectable pleiotrophin, either by silver staining or immunoblot analysis. Importantly, this bead depleted fraction was no longer capable of inducing UB, WD, or UB and WD branching morphogenesis. Insect cell-derived recombinant human pleiotrophin is incapable of inducing proliferation and experiments using recombinant human pleiotrophin produced in the insect cell line (R&D systems) was also unable to induce UB, WD, or UB and WD branching morphogenesis.

Example 5

During the course of purification, differences in the morphology of the branching UB, WD, or UB and WD, depending upon the amount of pleiotrophin present in the fraction (detected by immunoblotting) was observed. This was examined more carefully using the purified protein in which the pleiotrophin concentration was determined by immunoblotting using recombinant human pleiotrophin as a standard. High concentration ($\geqq 5$ µg/ml) pleiotrophin resulted in robust proliferation with less elongation, while lower concentrations of pleiotrophin (156 ng/ml-2.5 pg/ml) induced dichotomous branching and elongation of the stalk, similar to that seen with whole BSN-CM.

Example 6

In the course of purification, variation in the inductive capacity of whole BSN-CM on UB, WD, or UB and WD branching was encountered. It was found that the addition of fibroblast growth factor1 (FGF1) could potentiate the activity of the BSN-CM, although alone or in combination with GDNF it was not sufficient to induce isolated UB, WD, or UB and WD branching morphogenesis. Based on this finding, the growth media (either BSN-CM or individual fractions) used in the culture of the isolated UB, WD, or UB and WD was supplemented with 250 ng/ml of FGF1. However, it was found that purified pleiotrophin supplemented with GDNF was capable of inducing UB, WD, or UB and WD branching morphogenesis in the absence of FGF1, although the UB, WD, or UB and WD grew faster when FGF1 was added to the culture.

This result suggests that pleiotrophin and GDNF alone are necessary and sufficient for the observed branching morphogenesis of the isolated UB, WD, or UB and WD, though a FGF-like activity could play a role in the process.

Example 7

Pleiotrophin also induces branching morphogenesis of UBs, WDs, or UBs and WDs in three dimensional culture. As discussed herein, E11 S mouse UB, WD, or UB and WD derived cells (UBs, WDs, or UBs and WDs) develop into branching tubular structures with lumens in the presence of BSN-CM. DNA array, PCR analysis, and immunostaining have confirmed the epithelial and UB, WD, OR UB AND WD-like characteristics of these cells. Using this model for UB, WD, or UB and WD branching morphogenesis, pleiotrophin was also capable of inducing the formation of branching structures of UBs, WDs, or UBs and WDs. As in the isolated UB, WD, or UB and WD culture model, the extent of UB, WD, or UB and WD branching morphogenesis was found to be concentration-dependent, with higher concentrations resulting in more extensive growth and branching. Morphologically, the structures were comparable to those induced by whole BSN-CM.

Example 8

Pleiotrophin is expressed in the embryonic kidney and secreted from MM derived cells but not UB, WD, or UB and WD-derived cells. By immunoblot, pleiotrophin was found in an extract of whole embryonic day 13 rat kidney. To determine whether epithelial cells or mesenchymal cells secrete pleiotrophin, conditioned medium derived from the UB, WD, or UB and WD cell line and the BSN cell line were compared. Only BSN-CM contained pleiotrophin. This is consistent with a previous in situ hybridization study (Vanderwinden et al., Anat. Embryol (Berl) 186:387-406, 1992), which showed that the developing rat kidney mesenchyme (as early as E13 of development) expresses pleiotrophin mRNA, but the ureteric bud, Wolffian duct bud, or ureteric and Wolffian duct bud does not. Another study had suggested the presence of pleiotrophin in the basement membrane of epithelial tubules in the developing kidney of E13 mouse embryos (Mitsiadis et al., Development 121:37-51, 1995). When frozen sections of mouse E 13 kidneys stained with anti-pleiotrophin antibodies were examined, a strong signal was observed in the basement membrane of the UB, WD, or UB and WD with weak staining in the surrounding MM. Since the MM expresses pleiotrophin mRNA at the earliest stages of kidney development (Vanderwinden et al., 1992), the data presented herein suggest that pleiotrophin is secreted by the MM and binds to the basement membrane of the UB, WD, or UB and WD where it can exert its morphogenetic function.

Example 9

Exogenous pleiotrophin affects UB, WD, or UB and WD morphology in embryonic kidney organ culture. While the spatiotemporal expression pattern and in vitro data from the isolated UB, WD, or UB and WD and the UB, WD, or UB and WD cell culture model strongly support a direct role for pleiotrophin in UB, WD, or UB and WD morphogenesis, it was also important to determine its effect in a system that more closely approximates the intact developing kidney. To study this pleiotrophin was applied to whole embryonic kidney organ culture. Exogenously added pleiotrophin disproportionately stimulated growth of the UB, WD, or UB and WD. Pleiotrophin-treated kidneys exhibited an expanded UB, WD, or UB and WD area in a concentration-dependent manner similar to that seen in the isolated UB, WD, or UB and WD culture. Furthermore, the central area of UB, WD, or UB and WD expansion became more prominent at higher concentrations of pleiotrophin. The whole kidney also appeared slightly larger following pleiotrophin treatment. Nephron induction visualized with PNA lectin appeared to be normal even in the presence of high concentrations of pleiotrophin. Thus, not only isolated UB, WD, or UB and WD, but also the UB, WD, or UB and WD in the context of the whole embryonic kidney responded to pleiotrophin, supporting the notion that the UB, WD, or UB and WD is the target for pleiotrophin action in the developing kidney.

Based upon this data an essential role for direct contact between the metanephric mesenchyme (MM) and the ureteric bud, Wolffian duct bud, or ureteric and Wolffian duct bud (UB, WD, or UB and WD) during metanephrogenesis was suggested. Induction of the isolated MM was inhibited by the placement of a filter with c 0.1 µm pore size between an inducer and the MM, suggesting an absolute requirement for cell contact between the MM and an inducer. However, a combination of soluble factors elaborated by an immortalized UB, WD, or UB and WD D cell line supplemented with either fibroblast growth factor (FGF)-2, or a combination of FGF2 and transforming growth factor are sufficient, in the absence of direct contact between the UB, WD, OR UB AND WD and MM, to induce the mesenchymal-epithelial transition and differentiation of the proximal nephron in cultures of isolated MM. Likewise, soluble factors produced by a MM cell line (BSN cells) supplemented with glial cell-derived neurotrophic factor (GDNF) have been suggested to be necessary and sufficient to induce extensive branching morphogenesis of the UB, WD, or UB and WD. Thus, soluble factors play a key role in both aspects of the mesenchymal-epithelial interaction leading to the formation of a functionally mature kidney. This constitutes an important revision in thinking relating to kidney organogenesis.

The identification of specific soluble factors (e.g., MM-derived soluble factors) mediating UB, WD, or UB and WD branching morphogenesis remains a central question in this field. Hepatocyte growth factor (HGF) has been shown to induce the formation of branching tubular structures with lumens in three-dimensional cultures of epithelial cell lines derived from adult kidneys (i.e., MDCK and mIMCD cells) (Barros et al., 1995; Cantley et al., 1994; Montesano et al., 1991; Santos et al., 1993). However, incubation of three-dimensional cultures of an embryonic cell line derived from the UB, WD, or UB and WD (UBs, WDs, or UBs and WDs) with HGF had a slight morphogenetic effect and the formation of branching tubular structures with lumens was not observed (Sakurai et al., 1997). Furthermore, HGF, alone or in the presence of GDNF, does not induce branching morphogenesis of the isolated UB, WD, or UB and WD (as seen with the MM cell conditioned medium).

Example 10

When BSN-CM was treated with trypsin or exposure to prolonged heat (100° C.; 30 min), the morphogenetic activity for the UB, WD, or UB and WD was completely abolished. Based on this result, it is likely that the morphogenetic factor(s) in BSN-CM is proteinaceous in nature.

Centrifugation filtration systems with different nominal molecular weight cutoffs were used to concentrate BSN-CM. Centricon™ filters with a 8 kDa molecular mass cutoff membrane maintained biological activities in the retained fraction but not in the flow-through, suggesting the morphogenetic activity is larger than 8 kD.

Example 11

As discussed, the morphogenetic factor is heparin binding. Thus, a heparin binding-column (Hitrap Heparin™, Amersham-Pharmacia) was employed. Each fraction was assayed in isolated UB, WD, or UB and WD culture system in the presence of GDNF and FGF-1. Strong proliferative/morphogenetic activity was observed in the fractions eluted with 0.9-1.25 M NaCl. These morphogenetically active fractions were adjusted to 1.7 M ammonium sulfate and were applied to the Phenyl Sepharose column at pH 7.2. Isolated UB, WD, or UB and WD culture showed that several different activities were present in fractions eluted between 1.5-0.7 M ammonium sulfate, The 1.5-1.35 M eluate fraction in FIG. 10 induced UB, WD, or UB and WD proliferation but had little effect on branching tubule formation or elongation. In contrast, the 0.9-0.7 M eluate exhibited branching morphogenesis and elongation, but less robust proliferation. Interestingly, the activity found in fractions 7-9 suggested a combination of both fraction 6 and 10. This result suggests that although full-blown branching morphogenesis (as seen in the UB, WD, or UB and WD culture in fraction 9) may require a combination of multiple factors (e.g., a proliferative factor present in fraction 6 plus a possible elongation/branching factor present in fraction 10), individual factors can be separated and purified. In fact, by SDS-PAGE and silver staining, fraction 6, which appears to be mainly proliferative, contains a few bands clustered between 18-31 kDa, while fraction 10, which appears to promote elongation and branching, contains one band visible at 31 kDa.

Example 12

Sequential use of a hydrophobic interaction column, a cation exchange column, and a gel filtration column lead to the purification of PTN from these heparin-bound active fractions. However, as discussed above, BSN-CM is likely to contain more than one morphogenetic factors. In fact while higher salt eluate fractions (fraction 6) from phenyl sepharose column contained PTN by western blotting, lower salt eluate from a phenyl sepharose column (fraction 10) did not. In addition, when morphogenetically active fractions eluted from a heparin column (adjusted to Tris HCl buffer pH 8.0) were applied to an anion exchange (Q) column, morphogenetic activity was eluted at 0.15-0.5 M NaCl fractions (4 and 5). This morphogenetic activity was preserved after applying these fractions to a gel filtration column. This Q column-bound activity is unlikely to be PTN because PTN (pI=9.3) should not bind to the Q column at pH 8.0. By microsequencing analysis, a heparin binding growth factor heregulin was present in these fractions. This result was further confirmed by western blotting, which was positive for heregulin alpha in these fractions. Recombinant human heregulin alpha (250 µg/ml) induced isolated UB, WD, or UB and WD to grow to the similar morphology as fractions 4 and 5 in the presence of GDNF and FGF1. Thus, it is very likely that heregulin is one of the factors that induce UB, WD, or UB and WD growth.

Example 13

Heparin-bound fractions of BSN-CM are likely to contain many morphogenetic growth-promoting factors other than PTN. Existence of such factors are highly likely for the following reasons: (1) an active fraction eluted from anion exchange (Q) column is not likely to contain PTN; (2) a fraction elated from a phenyl sepharose column at 0.7 M ammonium sulfate (fraction 10), which induced elongation and branching of the UB, WD, or UB and WD tubules, should not contain PTN. Considering the relatively low resolution of hydrophobic interaction column, the existence of very low concentrations of PTN cannot be excluded, however, a dose dependent response suggests that it is unlikely that such a low concentration of PTN can induce the UB, WD, or UB and WD morphogenesis observed; and (3) a morphogenetically active fraction containing little, if any, PTN by western blotting was obtained by sequential chromatography over 3 columns including a heparin sepharose column.

Example 14

Tissue culture media was obtained from Mediatech and bovine fetal calf serum was obtained from Biowhittiker. Growth factor reduced Matrigel™ and Type I collagen were obtained from Becton Dickenson. FGF1 and GDNF were obtained from R&D systems. FITC-conjugated DB were obtained from Vector Laboratories.

The Cellmax™ artificial capillary cell culture system was inoculated with BSN cells, and conditioned media harvested as described herein.

Isolated ureteric bud, Wolffian duct bud, or ureteric and Wolffian duct buds were obtained from whole embryonic kidneys as previously described. Briefly, the embryonic kidney was digested with trypsin and the UB, WD, or UB and WD separated from the MM using fine-tipped needles. The UBs, WDs, or UBs and WDs were suspended within a matrix containing growth factor reduced Matrigel™ and Type I collagen and buffered by HEPES, $NaHCO_3$, and DMEM to a pH of approximately 7.2. This mixture containing the suspended UB, WD, or UB and WD was applied to the top of the Transwell filter and BSN-conditioned media added to the well. The BSN conditioned media is supplemented with GDNF (125 ng/ml) and FGF1 (31 ng/ml) and 10% FCS, and the isolated UBs, WDs, or UBs and WDs cultured at 37° C. and humidified 5% $CO_2$ atmosphere. At specified time intervals, the cultured UB, WD, OR UB AND WD is separated from the surrounding matrix by blunt microdissection, sectioned into thirds, resuspended in new matrix and cultured with fresh supplemented BSN conditioned media.

Example 15

Isolated metanephric mesenchyme were isolated as described above and cultured on top of the Transwell filter.

DMEM/F12 media supplemented with FGF2 (100 ng/ml) and TGFa (10 ng/ml) was added to the well to prevent MM apoptosis.

Example 16

Using blunt microdissection with fine tipped needles, cultured or subcultured UBs, WDs, or UBs and WDs were cleanly separated from surrounding matrix and placed on top of a Transwell filter in close proximity to MM that was either freshly isolated or cultured. BSN conditioned media supplemented with GDNF, FGF1 and 10% FCS was added to the well.

Cultured or subcultured embryonic kidneys, isolated buds, and recombined kidneys were fixed in 4% paraformaldehyde and processed for immunofluorescent staining with either FITC-conjugated DB or antibodies. Immunofluorescence was detected with a Zeiss laser-scanning confocal microscope.

Example 17

Adult male rats (weighing200-250 grams) were housed and fed on standard rat chow, water ingestion and 12-hour cycles of light and dark. All animals were maintained and experiments conducted in accord with the National Institutes of Health (NM) Guide for the care and Use of Lab Animals.

Rats were anesthetized with an intraperitoneal injection of sodium pentobarbitol solution (50 mg/kg). The anesthetized animals were placed on a warming blanket and a midline abdominal incision made. Bilateral or unilateral occlusion of the renal pedicule were maintained for 40 minutes to induce ischemia and the incision temporarily closed until completion of vascular occlusion. If an arterial catheter was required for the experiment one was placed in the femoral artery and exteriorized in the dorsal scapular region. If ureteral catheters were necessary, they were placed and exteriorized. Upon completion of ischemic period, the arterial occlusion are removed, the incisions were sutured or stapled closed and the rats allowed to recover for designated reperfusion time.

Example 18

Injury was induced with either mercuric chloride or the antibiotic gentamicin. Mercuric chloride primarily induces injury and subsequent cell proliferation in proximal straight tubules (PST), whereas gentamicin predominantly injures proximal convoluted tubules (PCT). Gentamicin nephrotoxicity were induced by LP injections of 40 mg/ml in 0.9 percent saline, divided with three daily injections over two days for a total of 400 mg/kg. Mercuric chloride are administered at various doses (0.25, 0.5, 1.0 and 2.5 mg/kg). These doses have been reported to induce renal injury ranging from minimal to marked.

Example 19

To mimic the usual clinical situation, some rats were exposed to either gentamicin or mercuric chloride at the ischemic injury. The renal injury was especially severe in these animals.

To purify factors involved in embryonic nephrogenesis, BSN cell conditioned media (BSN-CM) was collected after 2 to 4 days of BSN cell confluency, spun at low speed to remove cell debris and filtered (0.22 µm filter). The media is then concentrated (Vivaflow™ 200, 5 kDA cutoff) subjected to sequential liquid column chromatography and ion techniques, and final purification accomplished with HPLC and SDS-Page electrophoresis. The final purified protein(s) was submitted for microsequencing to an out side vender.

Example 20

Isolated ureteric bud, Wolffian duct bud, or ureteric and Wolffian duct buds were obtained from whole embryonic kidneys as described herein. Briefly, the embryonic kidney was lightly digested with trypsin and the UB, WD, or UB and WD were separated from the MM using fine-tipped needles. The UBs, WDs, or UBs and WDs were suspended within a matrix containing growth factor reduced Matrigel™ and Type I collagen and buffered by HEPES, $NaHCO_3$, and DMEM to a pH of approximately 7.2. This mixture containing the suspended UB, WD, or UB and WD was applied to the top of the Transwell filter and the purified factor is applied to the well. The factor is supplemented with GDNF (125 ng/ml) and 10% FCS, and the isolated UBs, WDs, or UBs and WDs are cultured at 37° C. and humidified 5% $CO_2$ atmosphere and branching morphogenesis, was assayed.

Example 21

Plasma collections during the experiment were collected via the rat tail vein under isoflurane anaesthesia. A large blood volume was collected at the end of the experimental period by sanguination under pentobarbitol (50 mg/kg) anacstiesia. Plasma from these collections were analyzed for sodium, potassium, ionized calcium, ionized magnesium (Nova 8 Electrolyte Analyzer), BUN and crealinine by autoanalyzer (core facility). Urine collection during and at the end of the experiment were done in metabolic cages. The urine was analyzed colormetrically for creatinine, calcium, magnesium, phosphate and chloride and protein. Sodium and potassium are measured with a Nova 6 Electrolyte Analyzer.

Example 22

Cross sections of kidney from each rat were fixed on a microscope slide and stained with hematoxylin and eosin. Slides were read for the presence or absence of tubular epithelial degeneration and/or necrosis.

Example 23

Tubular injury and cell proliferation were assessed on PCNA/PAS sections. Staining was done on 5 µm paraffin sections from ethacam-fixed renal tissue. Proliferating cells were immunostained with a rabbit anti-mouse monoclonal antibody (PC 10 from Dako) directed to proliferating cell nuclear antigen (PCNA). After blocking (goat sera) and incubation with the primary antibody, the sections were incubated with biotinylated goat-anti rabbit antiserum in the presence of normal rat serum and stained by the avidin-biotinylated horseradish peroxidase complex (Vectastatin™, Vector Labs) using 3,3'-diaminobenzidine as the chromogen. Sections were then counterstained with methyl green and periodic acid-Schiff (PAS).

Example 24

Identification and determination of apoptosis was done using the terminal deoxynucleotidyl transferase (TdT)-mediated UTP biotin nick-end labeling (TUNEL) technique by using an Apoptag™ in situ apoptosis detection kit (Oncor, Gaitheburg, Md.). Frozen sections (5um) were fixed in 10% neutral-buffered red formalin and post fixed in ethanol: acetic acid at −20° C. for comparison to control tissue as described herein.

Example 25

Determination of the factor(s) was also performed in adult rat kidney: After purification of unique factor(s) an antibody was generated by immunizing rabbits with purified protein (Multiple Peptide Systems, San Diego, Calif.). Kidney homogenates following ischemic and/or nephrotoxin injury were fractionated on 4-15% SDS polyacrylamide gels under reducing conditions and transferred to PVDF membranes. After blocking with phosphate buffered saline containing 5% nonfat milk, the blots were incubated Primary antibody (rabbit anti-rat peptide) and visualized by enhanced chemiluminescence system (Pierce). If peptide was present by western blot analysis then the polyclonal was used for immunohistochemical detection and localization.

Example 26

Tissue culture media were obtained from Mediatech and bovine fetal calf serum (FCS) from Biowhittaker (East Rutherford, N.J.). Transwell filters, pore size 0.4 μm, were obtained from Costar (Cambridge, Mass.). Growth factor reduced Matrigel™ was obtained from Becton Dickenson (Franklin Lakes, N.J.). Glial-cell derived neutrophic factor (GDNF), fibroblast growth factor-1 (FGF1) and fibroblast growth factor-7 (FGF7) were obtained from R&D Systems (Minneapolis, Minn.). FITC-conjugated Dolicus Biflorous and rhodamine-conjugated peanut agglutinin (PNA) lectin were obtained from Vector Laboratories (Burlingame, Calif.).

The entire urogenital tract was isolated from timed pregnant Holtzman rats at embryonic day 13 (E13). Kidney rudiments were dissected, and the Wolffian duct was transected and removed. In some cases, the mesonephric tubules and most of the intermediate mesoderm were mechanically separated from the WD leaving a thin layer of the intermediate mesoderm that remained adherent to the WD. In some cases, the intermediate mesoderm was carefully stripped away in its entirety so that the epithelial tube of the WD remained intact. The WD with mesonephros and the WD with intermediate mesoderm were placed on 0.4 μm pore size Transwell filters and cultured at the air-media interface. The isolated WD devoid of all intermediate mesoderm was suspended in a matrix containing growth factor reduced Matrigel'm and DMEM/F12 (50:50 v/v) on a 0.4 μm pore sized Transwell filter. All cultures were carried out at 37° C. in a fully humidified 5% $CO_2$ atmosphere in the presence of DMEM/F12 (50:50) media supplemented with 10% fetal calf serum (FCS), GDNF (10 ng/mL for the WD plus mesonephros, 125 ng/ml WD plus mesoderm and isolated WD) and, if necessary, either FGF1 (250 ng/ml) or FGF7 (50 ng/ml).

Budded Wolffian ducts are removed from the filter and were lightly digested with trypsin, and the buds were separated from the Wolffian duct and surrounding attached cells. The microdissected in vitro-formed buds were suspended within a matrix containing growth factor-reduced Matrigel™ and DMEM/F12 (50:50 v/v) on a 0.4 μm pore sized Transwell filter and BSN-conditioned media (prepared as described previously (29)) added to the well. The BSN-CM was supplemented with GDNF (125 ng/ml) and FGF1 (250 ng/ml). These in vitro-formed UBs were then cultured at 37° C. in a humidified 5% CO2 atmosphere.

Optimization of Growth Factor and Matrix (Natural and Artificial) Conditions for Isolated Ureteric Bud Branching The entire urogenital tract was isolated from timed pregnant Holtzman rats at embryonic day 13 (E13). Kidney rudiments were dissected and lightly digested in trypsin for 15 minutes, after which the ureteric buds were mechanically separated from the metanephric mesenchyme. For the growth factor optimization, the buds were suspended within a matrix containing growth factor-reduced Matrigel™ and DMEM/F12 (50:50 v/v) on a 0.4 μm pore sized Transwell filter and BSN-conditioned media supplemented with 10% FCS and 1% antibiotics was placed beneath the filter. GDNF (125 ng/ml), FGF1 (250 ng/ml), FGF7 (50 ng/ml), HRG (500 ng/ml), PTN (purified from BSN-CM) was added to the media in various combinations to achieve a "minimal" and "most robust" growth factor condition. For the matrix optimization, isolated buds were cultured in a BSN-CM supplemented with 10% FCS, GDNF (125 ng/ml), FGF1 (250 ng/ml), and 1% antibiotics. Isolate buds were suspended in matrices (natural and artificial) consisting of growth factor reduced Matrigel™ diluted with DMEM/F12 (15%, 25%, 50%, 75% and 100%), type I collagen (3.0 mg/ml), Puramatrix™, 1% alginate solution (crosslinked with 100 mM $CaCl_2$), and type IV collagen (0.75 mg/mL). In some cases, type I collagen, laminin 1, alginate or type IV collagen were added to a 50% growth factor reduced Matrigel™ solution. All matrix solutions were supplemented with DMEM and buffered by HEPES and $NaHCO_3$ to a pH of approximately 7.2. The isolated buds were then cultured at 37° C. in a humidified 5% $CO_2$ atmosphere.

After 4-6 days the branched in vitro-formed UBs were separated from the surrounding matrix by blunt dissection. Branched buds with minimal matrix were placed on a 0.4 μm pore sized Transwell filter with DMEM/F12 (50:50) supplemented with 10% FCS in lower well. Metanephric mesenchyme from kidneys at embryonic day 13 was placed next to and on the branched in vitro-formed UB. After 4-7 days of culture, 37° C. and 5% humidified CO2, the recombined kidney-like tissues were fixed in 4% parafomaldehyde, extensively washed in PBS and processed for fluorescent staining.

Tissues were fixed with 2% paraformaldehyde for 30 min at 4° C., blocked with 50 mM $NH_4Cl$ overnight at 4° C., and followed by incubation with 1% gelatin in 0.075% Saponin for 30 min at 37° C. After two washes with Neuraminidase buffer (150 mM NaCl/50 mM sodium acetate, pH 5.5), tissues were incubated with Neuraminidase (1 unit/ml) for 4 hr at 37° C. and then with rhodamine-conjugated PNA (50 μg/ml) and fluorescent-conjugated DB (50 μg/ml) for 60 min at 37° C. Tissues were postfixed with 2% paraformaldehyde and viewed with a laser-scanning confocal microscope.

The E13 kidney tissues, E18 kidney tissues, adult kidney tissues, and recombined kidney-like tissues were dissolved in lysis buffer and the RNA was isolated using the RNAqueous™ Micro kit from Ambion (Austin, Tex.). RNA was submitted to the UCSD Genechip core facility for processing with the Affymetrix (Santa Clara, Calif.) rat 230 2.0 whole genome chip. The in vivo time points were analyzed in biological triplicates, while the recombined tissues were analyzed in biological duplicates. All gene expression analysis was performed using Agilent (Santa Clara, Calif.) Genespring™ GX 7.3 software.

Recombined tissues on culture day 6 were gently detached from Transwell filter, and suspended within cold L-15 medium. The abdominal cavity of an adult male rat was opened under inhalant anesthesia with isoflurane. A subcapsular tunnel was prepared on the right kidney using the tip of microsurgery forceps. 2-6 recombined tissues were inserted into the subcapsular region together with a small volume of L-15 medium (~40 μl) by micropipette. The abdominal cavity was closed by suturing muscle and skin layers. After survival time of 14 days, the kidneys with implants were excised and provided for histological analyses.

Host kidneys bearing implants were excised, fixed in 4% paraformaldehyde/0.1 M phosphate buffered saline, pH 7.4 for 24 hr at 4° C., and incubated within a graded concentration of sucrose solution (10%, 15%, and 20%). Samples were embedded in Tissue Tek O.C.T. compound (Sakura Finetek, Torrance, Calif.), and frozen rapidly. Cryosections were cut at a thickness of 4 μm by a Cryostat CM3050S (Leica, Heidelberg, Germany), pasted on slides and air-dried. The specimens were stained with a mixture of anti-rat PECAM-1 (CD31) antibody (1:100; clone TLD-3A12, mouse IgG1k, Pharmingen) and anti-collagen type IV antibody (1:100; rabbit polyclonal, Chemicon) at 4° C. overnight. Then they were reacted with a mixture of donkey anti-mouse IgG-Alexa Fluor 488, goat anti-rabbit IgG-Alexa Fluor 568, and 4',6-diamidino-2-phenylindole dihydrochloride (DAPI) at room temperature for 1 hr. Fluorescent labeled antibodies and DAPI were purchased from Molecular Probes (Eugene, Oreg.). The specimens were observed with a Nikon D-Eclipse C1 confocal laser scanning microscope. Some cryosections were processed for routine histology using hematoxylin and eosin (H&E) staining, and observed with a Nikon Eclipse TE300 light microscope.

The first developmental event exclusive to metanephric kidney development is the outgrowth of the UB from the Wolffian duct. Using three different methods, this developmental event was replicated in vitro (Table 1). First, the whole mesonephros was isolated and cultured on a Transwell filter in the presence of a media containing 10% serum and 10 ng/mL GDNF. After two days in culture, numerous budding events occurred at multiple foci along the WD (FIG. 1A, B). Note that, assuming a single focus of budding can yield a kidney (as occurs in vivo), if each of the multiple buds can be cultured individually, then there is the possibility of many kidneys arising from a single WD cultured in vitro. In the second method, the mesonephric tubules, along with most of the non-epithelial mesoderm, were removed from the WD prior to in vitro culture. For impressive budding to occur, the GDNF concentration had to be increased to ~125 ng/mL and an additional growth factor was required; either FGF1 at ~250 ng/mL or FGF7 at ~50 ng/mL (FIG. 1C, D). In the third method, WD was completely cleared of all surrounding mesoderm prior to in vitro culture, leaving essentially an epithelial tube. In this "minimal" system, budding could not be achieved in 2D Transwell culture. Rather, the WD had to be suspended in a 3D gel composed of diluted Matrigel™ and then cultured in a medium containing 125 ng/mL GDNF and either 250 ng/mL FGF1 or 50 ng/mL FGF7 (FIG. 1E, F). With all methods, although the overall surface area of the WD increases due to budding at multiple foci, the WD does not appear to lengthen significantly under any of the culture conditions.

TABLE 1

Wolffian duct budding conditions of Table 2. Growth factor effects on ureteric bud survival, growth and shape

| Dissected WD condition | Factors Necessary for Bud Formation |
| --- | --- |
| Whole Mesonephros | 2D filter culture, 10 ng/ml GDNF |
| WD + intermediate mesoderm | 2D filter culture, 125 ng/ml GDNF + 50 ng/ml FGF7 |
| | 2D filter culture, 125 ng/ml GDNF + 250 ng/ml FGF1 |

TABLE 1-continued

Wolffian duct budding conditions of Table 2. Growth factor effects on ureteric bud survival, growth and shape

| Dissected WD condition | Factors Necessary for Bud Formation |
| --- | --- |
| Clean WD (no intermediate mesoderm) | 3D-matrix (Matrigel), 125 ng/ml GDNF + 50 ng/ml FGF7 |
| | 3D-matrix (Matrigel), 125 ng/ml GDNF + 250 ng/ml FGF1 |

Figure 2:
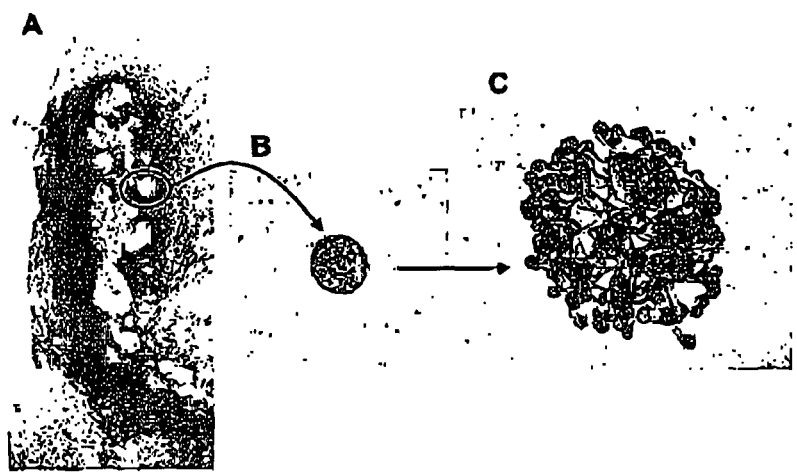
FIGS. 2A-C shows a method of Wolffian duct budding to isolated in vitro-formed UB branching. One bud from a budded Wolffian duct after 4 days in culture (A) can be excised, suspended in a gel (B), and induced to branch (C). This demonstrates how one Wolffian duct progenitor tissue can lead to the creation of multiple branched in vitro collecting ducts.

The next step in kidney development after WD budding is UB branching. It has previously been shown that rat isolated ureteric buds suspended in extracellular matrix gels undergo robust branching in the presence of GDNF and BSN-conditioned medium (secreted by metanephric mesenchyme-derived cells). The invention demonstrates in vitro-formed UB (created as described herein) retained the ability to undergo branching similar to newly isolated ureteric buds. FIG. 2 indicates how one bud was excised from the budded Wolffian duct and then induced to branch in 3D culture using culture conditions similar to those described for the "T-shaped" UB dissected from E13 rats. Thus, the in vitro-formed UBs, while not achieving the T-shaped structure assumed to be necessary for normal development of the kidney based on knockout studies, can grow and branch in vitro in a fashion similar to the excised T-shaped bud. This indicates that the T-shaped bud stage can be bypassed in the developmental strategy for tissue engineering. This also demonstrates how one Wolffian duct can be used to generate multiple ureteric buds, each capable of undergoing in vitro branching. Assuming that the branching UB-like structures can somehow be induced to form full nephrons, this potentially represents a point at which multiple renal tissues can be generated from a single WD.

Following the determination that the bud extracted from an in vitro budded Wolffian duct retains branching ability, the invention demonstrates the degree to which one could optimize branching with soluble factors to more closely resemble in vivo branching morphogenesis and to increase the extent of branching since each tip represents another potential point of propagation to create multiple renal tissues. Within the array of positive and negative growth and sculpting factors that comprise BSN-CM, pleiotrophin (PTN) has been identified as a significant branch-promoting factor. Several fibroblast growth factors (FGFs) can affect growth patterns of the isolated UB in the presence of BSN-CM and GDNF. Furthermore, heregulin (HRG) has recently been isolated from BSN-CM, which has been shown to induce non-branching, GDNF-independent growth of the isolated UB.

Figure 3:
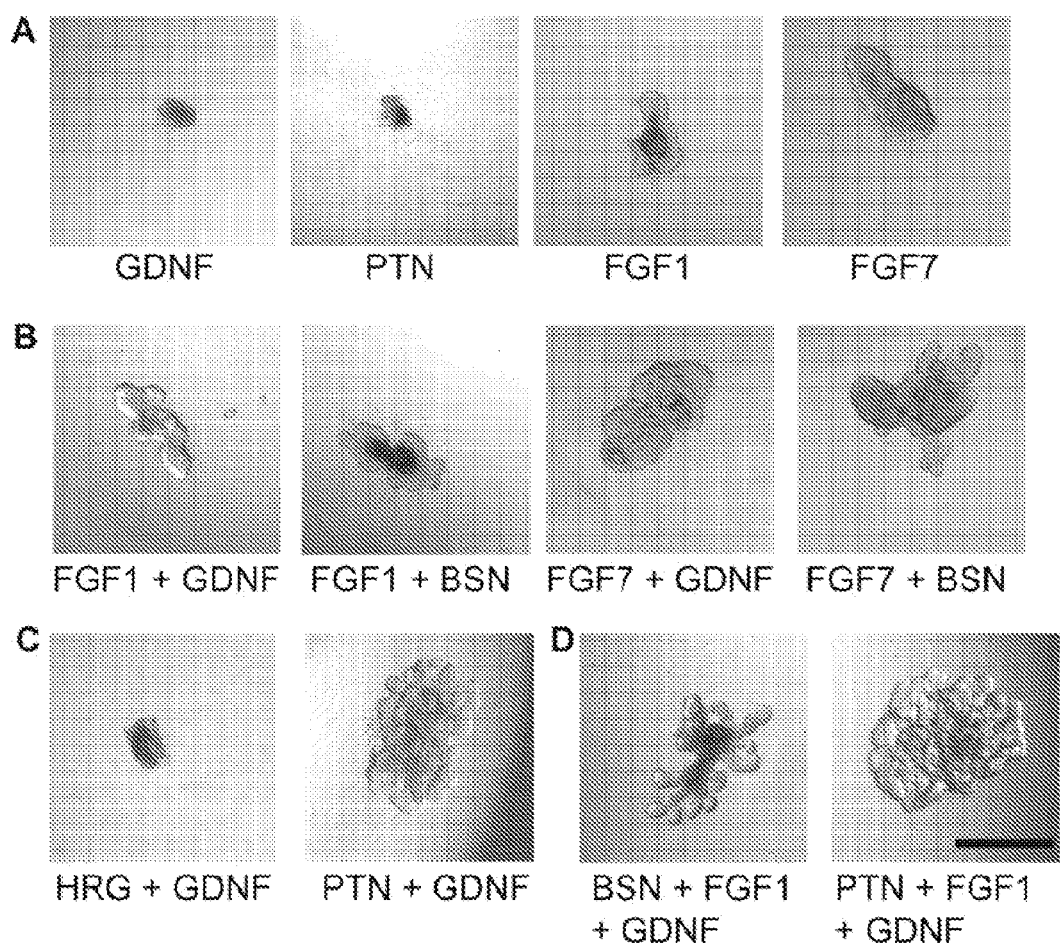
FIG. 3 shows an effect of soluble factors on isolated ureteric bud growth and shape and growth in 3D. Rat E13 ureteric buds were suspended in extracellular matrix gels comprising growth factor reduced Matrigel™ and Type 1 Collagen in the presence of the growth factors indicated. Pictures were taken at 4-6 days of culture. Pleiotrophin (PTN) was purified from BSN-CM. Concentrations used were GDNF 125 ng/ml, HRG 500 ng/ml, FGF1 250 ng/ml, FGF7 50 ng/ml. Scale bar corresponds to 500 µm.

The goal was to identify a growth factor (or a combination of a few defined factors) that reproduced the most robust branch-inducing conditions. Initially, the effect of a single soluble factor on growth of the isolated UB was examined. Consistent with previous reports, GDNF, PTN, HRG, or whole BSN-CM did not support growth of the isolated UB by itself, while FGFs supported survival and minimal growth (FIG. 3A and Table 2). Next, additional growth factors were added to the culture medium containing at least one fibroblast growth factor to enhance survival. Addition of every factor tested (including GDNF, PTN, HRG, and whole BSN-CM) to FGF1 or FGF7 stimulated growth of the isolated UBs to a much greater extent than each FGF alone. In addition, UB growth patterns were not altered significantly by addition of the second growth factor to either FGF-1 or FGF-7 (FIG. 3B). Combinations of 2 factors were also tested that, in isolation, were incapable of inducing UB growth. The invention demonstrates that the combination of PTN and GDNF (in the absence of FGFs) could induce branching growth of the isolated UB (FIG. 3C) and that whole BSN-CM and GDNF could also induce branching growth, although less reliably.

TABLE 2

Growth factor analysis on ureteric bud survival, growth and shape

|  | UB survival | Overall growth | Shape |
|---|---|---|---|
| BSN-CM | − | NA | NA |
| GDNF | − | NA | NA |
| HRG | − | NA | NA |
| PTN | − | NA | NA |
| FGF1 | + | + | tubular |
| FGF7 | + | ++ | globular |
| BSN + GDNF | − (Rarely +) | If survives ++ | If survives, branching |
| HRG + GDNF | − | NA | NA |
| PTN + GDNF | + | +++ | branching/globular |
| FGF1 + GDNF | + | +−++ | tubular |
| FGF7 + GDNF | + | +++ | globular |
| BSN + FGF1 | + | + | tubular |
| HRG + FGF1 | + | ++ | dilated tubular |
| PTN + FGF1 | + | + | tubular |
| BSN + FGF7 | + | +++ | globular |
| HRG + FGF7 | + | +++ | globular |
| PTN + FGF7 | + | +++ | globular |
| BSN + FGF1 + GDNF | + | +++ | branching tubular |
| HRG + FGF1 + GDNF | + | ++ | dilated tubular |
| PTN + FGF1 + GDNF | + | +++−++++ | branching/globular |
| BSN + FGF7 + GDNF | + | ++++ | globular |
| HRG + FGF7 + GDNF | + | ++++ | globular |
| PTN + FGF7 + GDNF | + | ++++ | globular |

Added FGF-1, a branching facilitating FGF, to other conditions that supported variable degrees of branching, including PTN plus GDNF and BSN-CM plus GDNF. The combination of PTN, FGF1, and GDNF sometimes induced excessive tip formation, and resulted in stalk-less UBs (FIG. 3D), while the combination of whole BSN-CM, FGF1, and GDNF induced the most robust branching growth of isolated UBs in terms of both tip and stalk formation. It should be noted that PTN had to be purified from mammalian sources (BSN-CM, 3T3-CM, or PTN cDNA transfected mammalian cell conditioned medium) in order to be biologically active in this assay.

Figure 4:
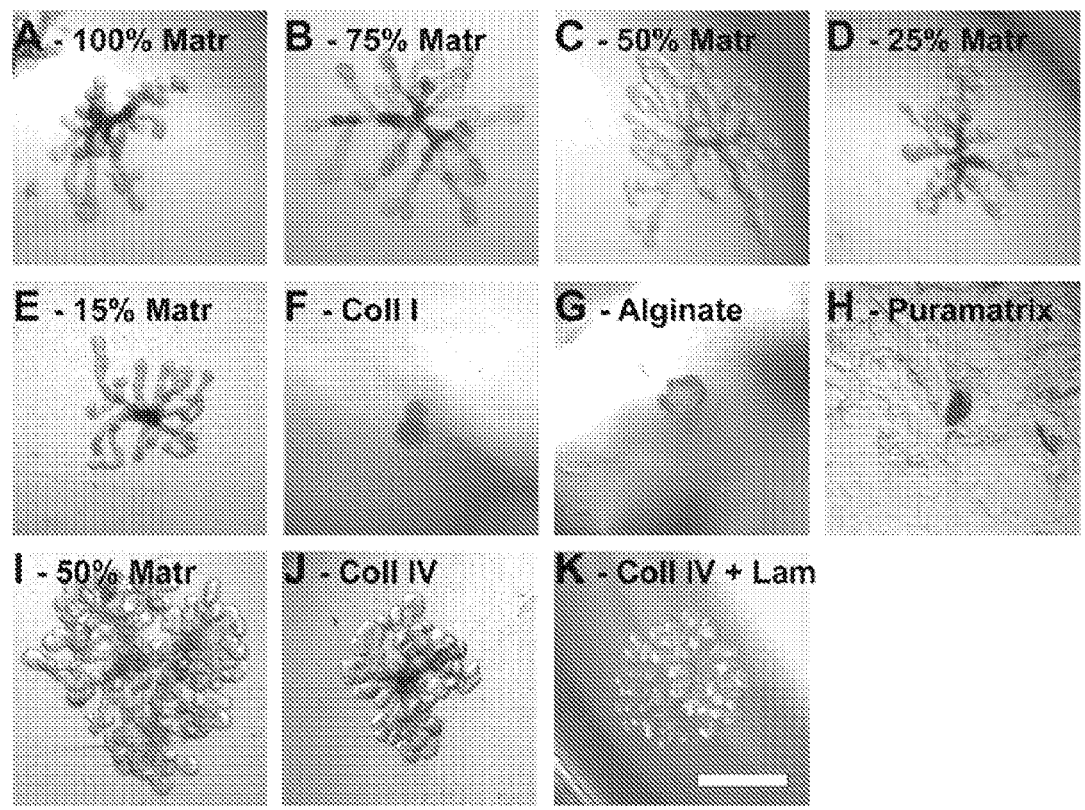
FIGS. 4A-I depicts the effects of extracellular matrix conditions on ureteric bud branching. (A) 100%, (B) 75%, (C) 50%, (D) 25%, (E) 15% Matrigel'm solutions. 3.0 mg/mL type I collagen (F) and the inert gels, 1% Alginate (G) and Puramtrix™ (H), did not support branching. Type IV collagen (0.75 mg/mL) alone could support branching morphogenesis (J) with no increases by the addition of laminin (0.33 mg/mL type IV collagen, 0.67 mg/mL laminin) (K), but were both less branched the 50% Matrigel™ control (I). All pictures taken after 7 days in culture. Scale bar corresponds to 500 µm.

Given that the extracellular matrix plays a significant role in terms of scaffolding for isolated UB growth and branching as well as modulation of growth factor effects, optimization of the growth conditions for 3-dimensional ureteric bud branching was then performed. Previous studies of isolated UB branching utilized a matrix of "growth-factor reduced" Matrigel™ and Type I collagen (50:50 v/v) supplemented with DMEM and buffered by HEPES and NaHCO$_3$ to a pH of approximately 7.2. First, it was determined whether Matrigel™ or type I collagen alone could support branching morphogenesis. FIG. 4 shows that type I collagen does not support branching morphogenesis and is, in fact, inhibitory, while Matrigel™ supports branching at a wide range of concentrations with decreases in branching at the highest and lowest concentrations (100% and 15%, respectively). In addition to the two original components, a 1% alginate solution, crosslinked with 100 mM CaCl$_2$, and Puramatrix', an inert self assembling peptide matrix, were also tested with the isolated UB system; neither supported UB branching.

Given that the mature kidney basement membrane is composed of approximately 50% type IV collagen and the network forming component of Matrigel™ is type IV collagen, other types of collagen were tested to see if type IV collagen alone could support branching morphogenesis or if the additional basement membrane components, such as laminin I, were also necessary. Surprisingly, type IV collagen alone did support branching morphogenesis, and additional factors such as laminin I did not increase branching capacity (FIGS. 4I-K). However, ureteric buds in type IV collagen do not grow as well as those in Matrigel™; this may be due to the fact that Matrigel™ contains a concentration of type IV collagen (~3.3 mg/mL) more than triple that of the pure type IV collagen commercially available (~1 mg/mL). These data demonstrate that in vitro isolated UB branching morphogenesis is dependent upon Collagen IV and does not require additional matrix components. A summary of all matrix effects is provided in Table 3.

TABLE 3

Extracellular matrix effects on ureteric bud development

| Network forming Matrix Molecules | Branching Support |
|---|---|
| Matrigel (15-100%) | Supports branching |
| Type IV Colagen (0.75 mg/mL) | Supports Branching |
| Type I collagen (0.4-4.0 mg/mL) | Does not support branching |
| Alginate (0.3-1.5%) | Does not support branching |
| Puramatrix (50-100%) | Does not support branching |

| Matrigel Matrix Additions | Effect on Branching |
|---|---|
| Laminin (0.2-0.75 mg/m) | No effect |
| Alginate (0.1-0.9%) | Diminished branching |
| Type I Collagen (0.4-3.0 mg/mL) | Diminished branching |
| Type IV Collagen (0.25-0.75 mg/mL) | No effect |

Taken together with the growth factor optimization studies, a minimal set of conditions can be defined for UB growth and branching as PTN plus GDNF in a type IV collagen matrix. The most robust system in terms of both tip and stalk formation, however, is BSN-CM supplemented with GDNF and FGF1 in a 50% Matrigel™ solution.

Figure 5:
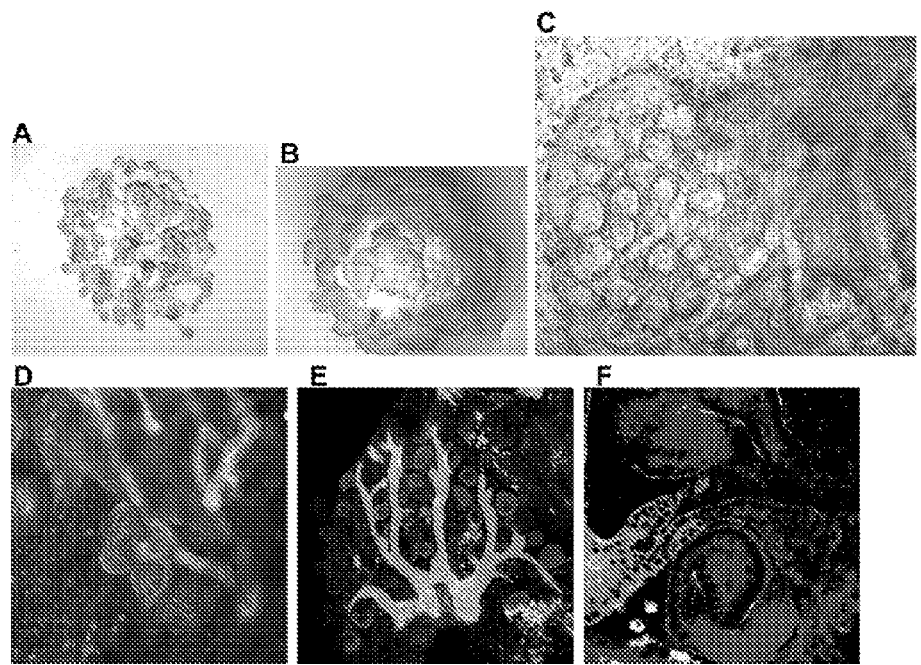
FIGS. 5A-F shows recombination of branched in vitro-formed UB with metanephric mesenchyme. The branched in vitro-formed UB (A) was mechanically separated from the matrix and recombined with freshly dissected undifferentiated MM (B). Recombined tissues were grown for approximately 4 to 7 days. During this time, the in vitro-formed UB continued to branch and invade the MM. The MM simultaneously was induced to undergo epithelial transformation (C). A 10× dual fluorescent micrograph of the recombined tissues stained with FITC-labeled *D. biflorus* and rhodamine-conjugated peanut agglutinin (PNA) lectin shows the mesenchymal to epithelial transition occurring around the UB branches (D,E-4×). A higher magnification (40×) at the fusion of the WD- and MM-derived epithelial cells demonstrates a contiguous tubule lumen (F).

Once a Wolffian duct has been budded in vitro and the dissected in vitro-formed UB has branched, the next step is to determine if 3D nephron formation can occur; the approach was to recombine the branched structure with fresh MM. These experiments differ from typical recombination studies with "T-shaped" UBs, considered a key developmental stage (32-34), in that the branched UB was derived from an in vitro budded Wolffian duct that does not form a T-shaped structure, as already described. The recombined tissue was cultured on a Transwell filter without any additional growth factors (FIG. 5B). Several days after recombination, branched structures had grown and elongated, and induction was evident by phase contrast microscopy (FIG. 5C). This was confirmed by confocal microscopy and lectin staining (FIGS. 5D-F). Connections between the collecting system and the more proximal portions of the tubule derived from the MM were evident.

Figure 6:
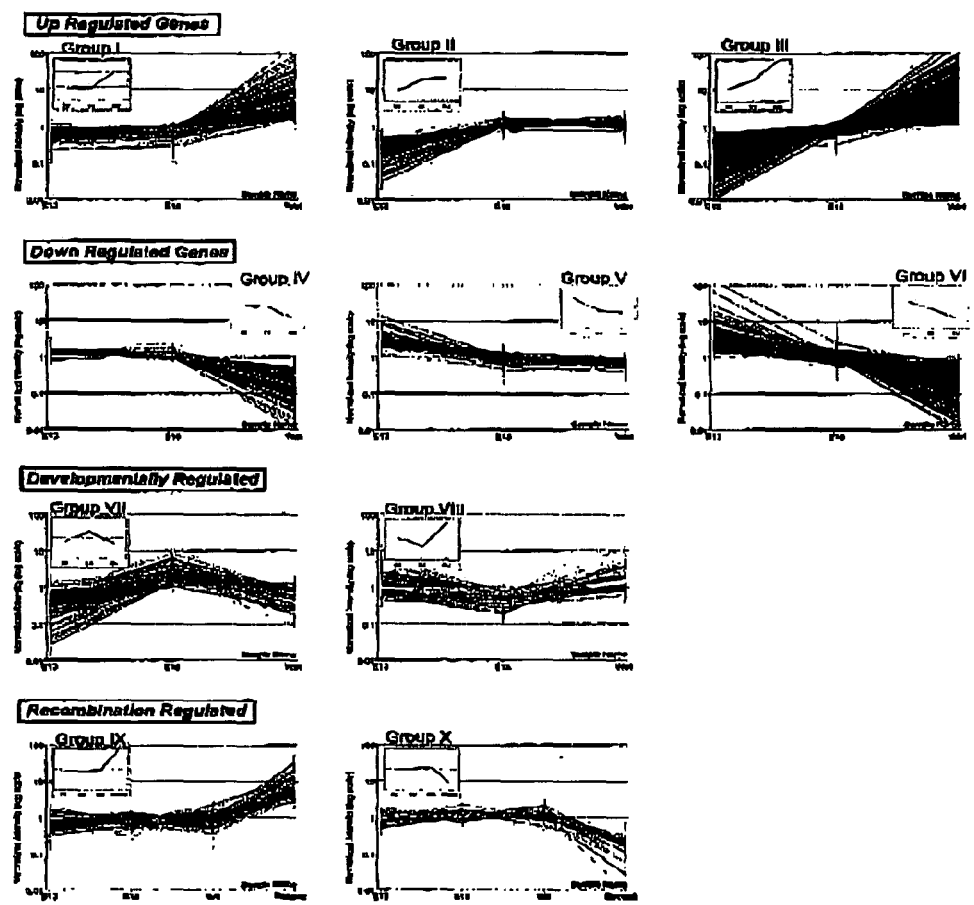
FIG. 6 shows grouping of the genes based on developmental expression patterns. Before the gene expression of the recombined tissue was analyzed, the genes on the chip were grouped according to their kidney developmental expression pattern. Up-regulated genes were defined as genes with 3 fold expression increases from E13 to Wk4. The genes were further grouped based on E18 expression level; if E18 was within 1.5 fold of E13 or Wk 4 then, the gene was defined as Group I or Group II, respectively. If E18 was in between those criteria then the gene was defined as Group III. An analogous grouping was performed for down-regulated genes. Developmentally regulated genes were defined as genes whose E18 expression was at least 3 fold higher or lower than E13 or Wk4 and 1.5 higher or lower than the other. Recombination regulated genes represent genes that were 3 fold higher or lower in the recombined tissue than all three developmental time points.

While the recombined tissues comprised of nephron structures resembling the late stages of renal development, it was important to verify the extent to which the MM and branched UB followed developmental pathways by analyzing the global gene expression and comparing it to the gene expression of early, late, post developmental kidneys. Genes with a 3-fold difference between any of the 4 conditions (E13, E18, Wk4, Recombined tissue) were analyzed. 6,763 genes from the Affymetrix 230 2.0 Rat gene chip fit that condition (genes flagged as "Absent" by the Affymetrix algorithm and genes without annotation were excluded from this analysis). The genes were organized into 10 groups based on their developmental expression patterns as described in FIG. 6 with 1,080 genes not fitting into any group. Then, the expression of each group of genes was analyzed in the recombined tissue to determine how far the recombined tissue gene expression had progressed relative to the three in vivo time points (See Table 4). Since the recombined tissue had progressed in vitro for seven days, the recombined tissue culture gene expression was hypothesized to reach a mid-to-late kidney developmental level similar to that of E17-E18 based on morphology. In rats, development is known to continue in the weeks following birth, so seven days of in vitro culture is not expected to recapitulate the gene expression pattern of the 4 week old kidneys. This comparison revealed that, while the in vitro engineered kidney-like tissues are not identical to any of the in vivo expression patterns, there is considerable resemblance to the in vivo gene expression of the E18 kidney. More than 50% of the genes that were up-regulated during the E18 time point were also up-regulated in the recombined tissue. In addition, almost 75% of the genes in Group VI properly down-regulated in the recombined tissue to at least E18 levels. This indicates that a large number of the developmental pathways are being properly regulated in the recombined tissue of what was originally the microdissected in vitro grown WD bud and fresh MM tissue. There also exists a group of genes that are absent or present at the onset of kidney development, followed by an up or down regulation during development, and then a return to their initial state following development (Groups VII and VIII respectively). These genes are present or absent during development, and, therefore, it is not possible to determine whether a particular gene is at the final or initial state. It can only be determined whether a gene is in a "developmental state" similar to E18. However, ~53% of the genes that were up-regulated at E18 were also up-regulated in the recombined tissue, further suggesting that many of the natural developmental pathways are being followed. Finally, there were genes that were abnormally high or low in the recombined tissue that did not change throughout development (these are genes in which the recombined tissue is at least 3 fold higher or lower than all three time points); these genes represented less than 5% of the total number of genes in the analysis, suggesting that the in vitro conditions cause few extraneous gene expression changes.

TABLE 4

Global microarray analysis of UB/MM recombination

| Up-regulated Genes | Percent of Recombination Genes that Up-regulated (Number of Genes) | Total Genes in Group |
|---|---|---|
| Group I | 13.19 (98) | 743 |
| Group II | 50.00 (82) | 164 |
| Group III | 49.76 (620) | 1246 |

| Down-regulated Genes | Percent of Recombination Genes that Down-regulated (Number of Genes) | |
|---|---|---|
| Group IV | 15.03 (196) | 1304 |
| Group V | 49.04 (51) | 104 |
| Group VI | 74.34 (762) | 1025 |

| Developmentally Up-regulated Genes | Percent of Recombination Genes that Up-regulated (Number of Genes) | |
|---|---|---|
| Group VII | 53.65 (169) | 315 |

TABLE 4-continued

Global microarray analysis of UB/MM recombination

| Developmentally Down-regulated Genes | Percent of Recombination Genes that Down-regulated (Number of Genes) | |
|---|---|---|
| Group VIII | 27.94 (126) | 451 |

| | Number of Genes |
|---|---|
| Recombo Abnormally High | |
| Group IX | 241 |
| Recombo Abnormally Low | |
| Group X | 90 |

Figure 7:
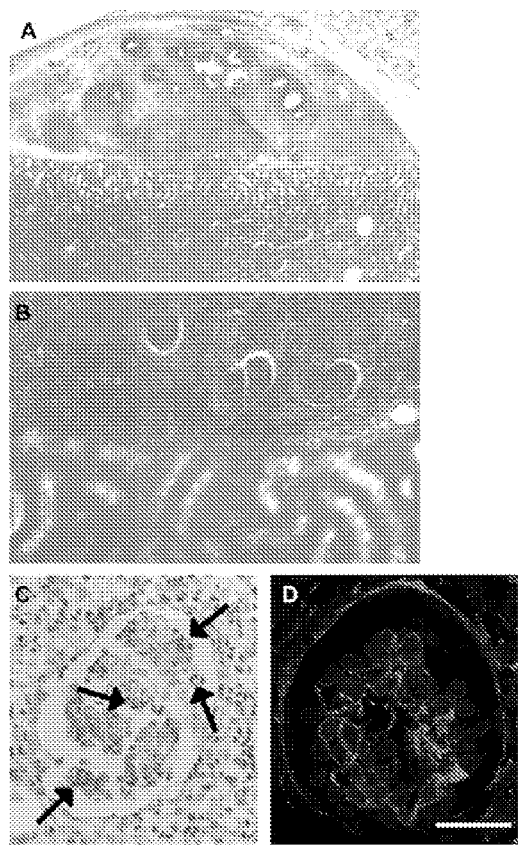
FIGS. 7A-D shows recombed tissue 14 days after implantation in to host rat. The recombined tissue has acquired blood vessels and developed glomeruli. (A) 4× (B) 20×. The presence of erythrocytes (arrow) in the glomeruli confirms blood flow in the recombined tissue—40× (C). The cells of the glomerulus express the endothelial marker, P-CAM1, and type IV collagen along its basement membrane (D)-60×. Scale bar corresponds to 50 μm.

In order for a kidney tissue to be functional it must contain a vasculature and glomeruli. While the microarray analysis demonstrated that the recombined tissue recapitulates many of the gene expression activities of renal development, few vascular genes were up-regulated, and, in any case, this does not predict whether the recombined tissue will be able to successfully integrate into a host animal and be functional. Previous studies have demonstrated that early avascular embryonic kidneys can be implanted into a host animal to obtain a vasculature with functional glomeruli. The recombined kidney-like tissue, which is derived from rat tissue, were implanted under the renal capsule of a host rat. After 14 days, the host animal was sacrificed and the implanted tissue was analyzed (FIG. 7). The implanted recombined tissue successfully recruited a vasculature, formed multiple glomeruli, and expressed the endothelial marker PECAM-1 in the cells of the glomerulus (FIG. 7D). Erythrocytes can be seen in the glomeruli of the recombined tissue indicating blood flow to the implanted tissue (FIG. 7C, arrows).

The disclosure provides a strategy for tissue engineering a propagatable kidney-like tissue by following key kidney developmental events in vitro in a stepwise fashion beginning with a Wolffian duct, essentially a single epithelial tube. The strategy results in tissues with spatially appropriate nephrons, glomeruli and a vasculature in three dimensions. Furthermore, optimization of each in vitro step was analyzed and provides details on a variety of conditions that can be used at each step, potentially offering multiple approaches within this strategy.

Figure 8:
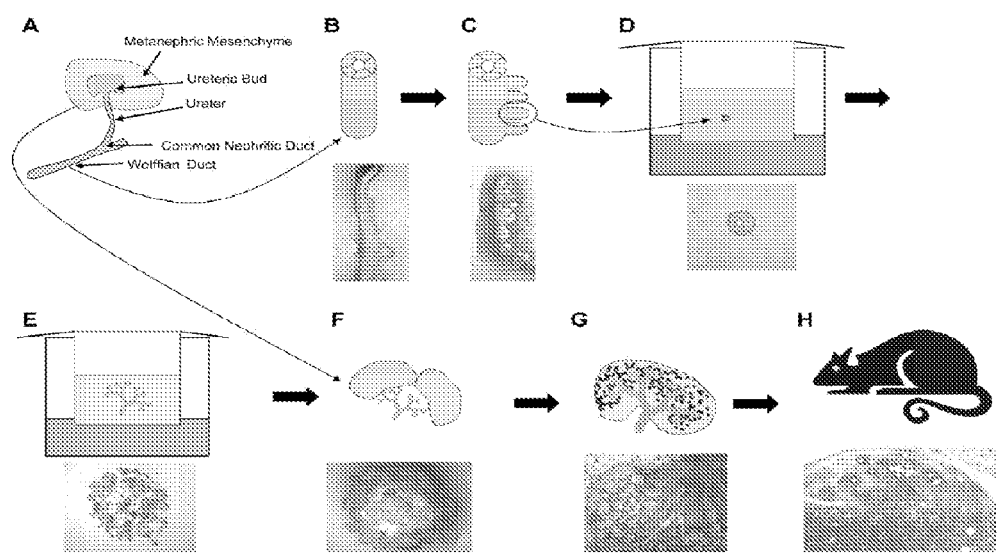
FIGS. 8A-E shows a general in vitro kidney engineering strategy. Overview of the steps to recapitulate kidney development in vitro. The Wolffian Duct is isolated (B) and induced to bud. Then, each bud can be isolated (D) and induced to undergo branching (E). The branched in vitro-formed UB is then recombined with metanephric mesenchyme (F) and after 4-6 days of mutual induction the recombined tissue resembles a late-stage embryonic kidney (G). The recombined tissue is then implanted into a host animal where it is vascularized and forms glomeruli (H).

FIG. 8 illustrates how these systems can be put together to create in vitro engineered renal structures from the initial components. This data also suggests the possibility of creating multiple 3D kidney-like tissues not only from a single Wolffian duct tissue, but, potentially, from an epithelial tubule consisting of relatively homogenous polarized epithelial cells in the presence of mesenchymal cells and/or tissues.

The optimization studies revealed that the Wolffian duct, the basic epithelial tubular structure from which the 3 dimensional collecting duct system of the kidney arises, requires only the presence of GDNF for budding if the whole mesonephros is cultured in vitro, but requires additionally either FGF-1 or FGF-7 if the mesonephric tubules and surrounding mesoderm are removed. Other factors, including those present in BSN-CM, can be employed as well. For example, activin inhibition has previously been demonstrated to promote budding, in place of FGF-1 or FGF-7. As shown here, a fully cleaned Wolffian duct, truly a polarized epithelial tube, requires a suspended culture system using a diluted Matrigel™ solution and the presence of growth factors in order to undergo budding in vitro. These experiments suggest that the surrounding mesoderm plays a role in budding by providing growth factors and/or necessary matrix components, which for tissue engineering purposes, are supplied exogenously here. Moreover, each of the many buds can be excised, suspended in a 3D matrix, and induced to undergo extensive branching morphogenesis. The branching in vitro-formed UB appears highly similar, if not identical, to the isolated UB in culture—both morphologically and in terms of functional ability to induce MM.

From the perspective of tissue engineering, beginning from a solitary epithelial tube, initial survival of the tubular cells is an obvious issue if multiple steps are involved. In the process of optimization of growth factors for the in vitro cultures, FGFs were the only soluble factors tested that supported both isolated WD and UB survival in vitro when applied as a single agent. However, another set of conditions that increased isolated UB survival was to simultaneous culture with PTN (or PTN-containing BSN-CM) and GDNF. In this case, branching was also observed. FGFs also affected the pattern of isolated UB growth. To achieve optimal branching growth, FGF-1, a growth factor that supports branching and growth of the isolated UB culture system, was combined with non-FGF branch-supporting growth factor combinations (i.e. GDNF plus either PTN or BSN-CM). In vitro, these growth factor conditions provided the most robust (i.e. growth plus most in vivo-like patterning) branch-stimulating conditions among the many soluble factor combinations that were tested. The fact that a combination of BSN-CM, FGF1, and GDNF gave more consistent branching growth than PTN, FGF1 and GDNF, suggests one or more factors within BSN-CM assist in culture. Conceivably these can include factors such as TGFβ-superfamily members, including bone morphogenetic proteins 2 and 4, which seem to modulate branching and are involved in sculpting of the isolated UB culture system. Thus, it is possible that a combination of PTN plus one additional "UB-sculpting factor" could replace BSN-CM to attain an ideal minimal set of conditions for a tissue engineering approach. The combination of BSN-CM, FGF1, and GDNF supports the most robust growth and branching of the UB in vitro.

Given the recent work on matrices and scaffolds for tissue engineering of bone, cartilage and other organs, both artificial and natural matrix conditions were analyzed for isolated 3D UB branching. The UB appears to only branch in type IV collagen or Matrigel™, which is type IV collagen based. Surprisingly, adding laminin I, which enhances branching of cultured cells, to a type IV collagen matrix did not further increase branching morphogenesis. This suggests that the initial extracellular matrix scaffold does not require all components of the final basement membrane and that the UB itself can synthesize any necessary supplementary proteins in an isolated system. In addition, two inert ECM molecules, Alginate, which has been used extensively in cartilage tissue engineering, and Puramatrix™, which was successfully used to support neuronal migration and promote osteoblast differentiation, were tested for branching support; the UB was unable to branch in either of these two artificial matrices. This may be caused by the inability of the UB to break down and remodel the artificial matrix to allow room for new branches. Nevertheless, an "ideal minimal system" for tissue engineering of the kidney according to the scheme ought to continue consideration of other artificial matrices as they become available.

The branched in vitro-formed UB, derived from the Wolffian duct, when placed adjacent to freshly isolated MM, resulted in mesenchymal-to-epithelial transformation and connections forming nephron-containing kidney tissues. This indicates the ability of the in vitro-formed UB, after being induced to branch in vitro, to be further manipulated in vitro to form kidney-like tissues. To determine the extent of similarity to the mid-to-late developing kidney in vivo, the recombined tissue was analyzed in microarray studies to reveal that more than 50% of the genes that up-regulated during kidney development also up-regulated in the recombined tissue. The comparison revealed that of the down-regulated genes, more than 72% of genes properly turn off. This suggests that the recombined tissue is following normal renal developmental pathways and creating nephron structures that not only phenotypically appear normal, but also resemble the transcriptome of the developing kidney.

While fresh MM tissue was used for the recombination step, this tissue is reported to contain pluripotent renal progenitor cells. It may be most feasible, however, to begin with cells alone. The BSN cell line is derived from the MM. The disclosure demonstrates the ability of secreted products from this cell line to induce optimal branching of the in vitro-formed UB (derived from in vitro WD culture) but thus far have been unable to show that the cells will recombine to form nephron-containing structures (data not shown). This may require a matrix-based strategy to make cells cohere or, alternatively, it is possible that these cells are too differentiated (perhaps more like mesenchymal "cap" cells) to be used for this application. Recently, it has been reported that mouse ES cells can be induced to form MM-like cells, suggesting an alternative approach.

Similar considerations apply to the creation of an epithelial tubule like the WD from cells. Of note, it has been shown that the UB cell line can form a tubule under conditions somewhat similar to those shown as optimal for branching of the isolated UB. It has also been shown that adult "progenitor-like" cells from the injured mouse kidney can form tubular epithelial structures in vitro and migrate to multiple compartments of the developing kidney in organ culture.

These types of cells, or possibly others that have recently been described that circumvent the use of and minimize concerns about embryonic tissue, may be more acceptable. The disclosure provides proof of concept for assembly of 3 dimensional renal tissues with differentiated nephron-containing structures from an epithelial tubule (the Wolffian duct), in whichever manner it is ultimately constructed. The methods may be suitable for xenogenic based approaches. Given the fact that they are tissue/organ culture-based, and that there are at least two points for propagation (at the level of the in vitro cultured WD and at the level of the in vitro-formed UB), it may be possible to "humanize" the tissue through transfection or similar strategies, or to induce expression of immunomodulatory or other genes to diminish the possibility of rejection and, potentially, improve functionality. These techniques, not currently feasible in mammalian adult organs, provide considerable flexibility for the goal of creating immunocompatible tissues suitable for a particular genetic profile.

Beginning with a single or limited in vitro propagatable tissue may also help address the concern about animal viruses with xeno-based approaches by creating a single or limited set of key points in a tissue engineering strategy where intense quality control or surveillance can be applied.

Vascularization was achieved by placing the recombined tissue in the in vivo setting of the renal capsule. The recombined tissue recruits a vasculature and forms glomeruli that appropriately express a key endothelial marker when implanted underneath the renal capsule of a host animal. Whether this technique will be successful as a therapy for ESRD is unknown, but again, it provides important "proof of concept" that an in vitro engineered kidney-like tissue, designed in the manner described herein, can survive and recruit a vasculature when placed in a host animal despite the absence of a developed renal vasculature of its own. Among the goals of kidney engineering are to design a kidney or tissue that can replace damaged kidneys and/or alleviate the problems associated with current allogenic transplants. The ability to begin with an epithelial tube, the stripped Wolffian duct, and take it in vitro to the point of vascularization represents an important result in considering how developmental strategies can be employed for the purpose of tissue engineering of the kidney. Moreover, this method allows for the creation of multiple recombined kidney-like tissues from a single Wolffian duct progenitor tissue or, potentially, a pluripotent epithelial tubule constructed from cells, whether adult, embryonic, amniotic or other. Embryonic-derived tissues seem to elicit a reduced immune response in rodents; therefore, in vitro manipulation of xeno-tissues or primitive cells to create kidney tissue may result in a less antigenic transplant than alternative options, such as whole embryonic kidneys that have had a longer time to develop in utero.

While many approaches are being taken towards engineering kidney substitutes, that a kidney-like tissue formed by following the natural developmental progression will be more likely to recapitulate the 3 dimensional relationships necessary to maintain vital renal functions as opposed to other cell-based kidney engineering approaches. The disclosure provides guidelines for such a strategy, at least in rodents, to stimulate renal progenitor tissues to follow the natural developmental path resulting in the in vitro engineered kidney-like tissue containing a branched collecting duct system, nephrons, glomeruli and a vasculature. That the strategy has strong potential for propagation of the engineered kidney-like tissue, as well as modulation of functionality and immunogenicity by transfection-type methods, adds to its potential.

An approximately 100 μm segment of WD was excised and suspended within the isolated MM from one kidney in a 1 mg/mL type I collagen solution (supplemented with DMEM and buffered by HEPES and NaHCO$_3$ to a pH of approximately 7.2). Before the gel was completely solidified, the WD segment was placed in the crevice of the MM left behind from the removal of the UB. The WD/MM tissue was cultured in the presence of a DMEM:F12 medium supplemented with 10% FBS (Hyclone™, Logan, Utah) and 1% antibiotics for 7 or 12 days. All cultures were incubated at 37° C. in a humidified 5% CO$_2$ and 100% humidity atmosphere.

Confluent monolayers of mouse SV40 large-T antigen transfected UB cells (Barasch) or inner medullary collecting duct (IMCD) cells (Rauchman) were trypsinized and suspended in DME/F12 (supplemented with 10% FBS and 1% antibiotics) at a concentration of 1×10$^5$ cells/mL. 20 μL of the cell solution was placed on the bottom of a Petri dish lid with 10 mL of PBS in the Petri dish. The cells were incubated as a hanging drop for 2 days at 37° C. in a humidified 5% CO$_2$ atmosphere. The cell aggregates were removed from the hanging drops and placed on a 0.4 μm Transwell filter surrounded by freshly isolated MM with 400 μL DMEM:F12 media supplemented with 10% FBS and 1% antibiotics placed below the filter and incubated for an additional 7 days.

The MM primary cell line was created by placing freshly isolated MM cells directly on a cell-culture treated plate. The MM cells were cultured on the plate for 5 days after which time the MM cells were trypsinized and placed on new plates. To create conditioned medium BSN, RIMM-18, MM primary, or 3T3 cells were cultured on plates and allowed to reach confluence. After confluence was reached, the medium was replaced with DMEM:F12 (no antibiotics or FBS) and the cells were incubated for 3 days. After 3 days the conditioned medium was removed and concentrated 5 times with a 5000 MW cutoff Millipore (Billerica, Mass.) filter.

Isolated ureteric buds were suspended in a growth factor-reduced Matrigel™ solution (1:1 Matrigel™:DMEM/F12), and cultured with conditioned medium from the BSN, RIMM-18, MM primary, or 3T3 cell lines supplemented with 10% FBS, 1% antibiotics, 125 ng/mL FGF1, and 125 ng/mL GDNF. The suspended UBs were then cultured for 7 days at which time tips were counted.

Embryonic metanephric kidneys were isolated and suspended in extracellular matrix solutions of type I collagen, type IV collagen, or growth factor-reduced Matrigel™ at the noted concentrations. All matrix solutions were supplemented with DMEM and buffered by HEPES and NaHCO$_3$ to a pH of approximately 7.2. Kidneys were cultured in the presence of 600 μL DMEM:F12 supplemented with 10% FCS and 1% antibiotics for 7 days.

After the indicated number of days, kidney cultures were fixed for 30 min with 4% paraformaldehyde in PBS. Fixed kidney cultures were rinsed with TBS and extracted in absolute methanol at −20° C. for 20 min. Samples were then blocked for 1 hr in 3% BSA in TBS-T at 4° C. followed by incubation in anti-E-cadherin, anti-cytokeratin, and/or anti-PAX-2 antibodies (1:500 in blocking solution) for 24 hr at 4° C. Samples were then washed 3×8 hr in TBS-T, followed by incubation in AlexaFluor594, AlexaFluor488 antibody (1:2000), and/or FITC-DB (1:500) for 24 hr at 4° C., and a final 3×8 hr washes in TBS-T at 4° C. Samples were then mounted on slides with ProLong Gold™ antifade reagent (Invitrogen, Carlsbad, Calif.). For PNA staining, following the blocking step the tissues were washed twice with Neuraminidase buffer (150 mM NaCl, 50 mM sodium acetate, pH 5.5), incubated with Neuraminidase (1 unit/ml) for 4 hr at 37° C. and then with rhodamine-conjugated PNA (50 μg/ml) and FITC-DB (1:500) for 24 hr at 4° C. Fluorescently stained samples were imaged using either the Nikon EZ-C1 confocal system.

Kidney cultures from HoxB7-GFP mice were fixed for 30 min with 4% paraformaldehyde in PBS and rinsed 3×5 min in PBS. Kidneys were then cleared with Focus Clear™ (Cedarlane Laboratories, Burlington, N.C.) for 20 min and mounted on depression slides with Mount Clear™ (Cedarlane Laboratories, Burlington, N.C.). Samples were imaged on the FV300 Olympus 2-photon microscopy system. 3D Reconstructions, isosurfacing, and 3D measurements of fluorescent stacks were performed using Image Pro Plus 3D Constructor 5.1 (Media Cybernetics, Bethesda, Md.). Tissue thickness was determined as being the minimum distance between two planes (or Feret minimum). Length to thickness ratio was calculated as the Feret maximum to Feret minimum ratio. Kidney volumes were estimated as the volume of an ellipsoid with the dimensions of half the length, depth and width of a bounding box around the branching structure. All samples were analyzed with n≧3 and with errors reported as the standard error of the mean.

To investigate whether an epithelial tube with an apparently homogenous cell population could function as a UB and retain the capacities to undergo branching morphogenesis and induce MET, the UB was removed from an E13 rat kidney and a segment of the WD from an E13 rat kidney was put in its place. The E13 kidney with the UB replaced by a segment of WD developed a branched collecting duct system and induced MM to epithelialize in a manner similar to that of traditional in vitro metanephric kidney culture. After 7 days of in vitro culture, convoluted MM-derived epithelial structures expressing E-cadherin were visible, suggesting the formation of nascent nephrons. After 12 days of in vitro culture, in addition to increased growth of the collecting duct system, a large number of developing glomeruli were evident by PNA lectin staining. This demonstrates that the epithelial tube of the WD can branch and form a collecting duct structure that induces MM epithelialization and glomerulus formation.

Since developmental approaches to tissue engineering begin with a homogenous epithelial tube, the next step was to attempt to construct an epithelial tube from a homogenous cell line possessing the potential to act as a UB or WD.

Initially, the process of constructing an epithelial tissue from cells was simulated using an immortalized mouse UB cell line. This cell line is capable of undergoing tubulogenesis in 3-dimensional extracellular matrix gels in response to a conditioned medium (CM) from a metanephric mesenchyme cell line (BSN cell line). To test whether these cells are capable of transforming into a UB tissue, the cells were induced to form cell aggregates by growing the cells in hanging drop cultures. The inductive and branching capacity of these UB cell aggregates was then tested by establishing a culture system in which the aggregates were combined with freshly isolated E13 rat MM. The UB cell aggregates not only induced mesenchymal-to-epithelial transition of the isolated MM cells, but connections between the UB cell aggregate and isolated MM were also found, suggesting that recombination of the MM with pre-formed aggregates of UB cells results in the formation of a contiguous tissue segment, reminiscent of the recombination of cultured isolated UB with MM (REF). For example, the E-cadherin positive/DB negative MM-derived tubule appears to be continuous with the D. biflorus (DB)-positive/E-cadherin positive UB-cell-derived structure. While the UB cell aggregate did not appear to branch (perhaps due to the lack of a 3-D ECM), polarized epithelial multicellular structures were observed.

A similar experiment was performed using the inner medullary collecting duct (IMCD) cell line, a cell line derived from the mouse adult collecting duct. This cell line is also capable of undergoing branching tubulogenesis in 3D ECM cultures. In contrast to UB cells, hanging drop aggregates of IMCD cells were capable of self-organizing into tubules with lumens following recombination with MM; additionally, although the IMCD cell aggregates did not induce the MM to form multiple long tubules with lumens as is the case with the UB cells, occasional formation of small comma-shaped bodies could be found.

Figure 12:
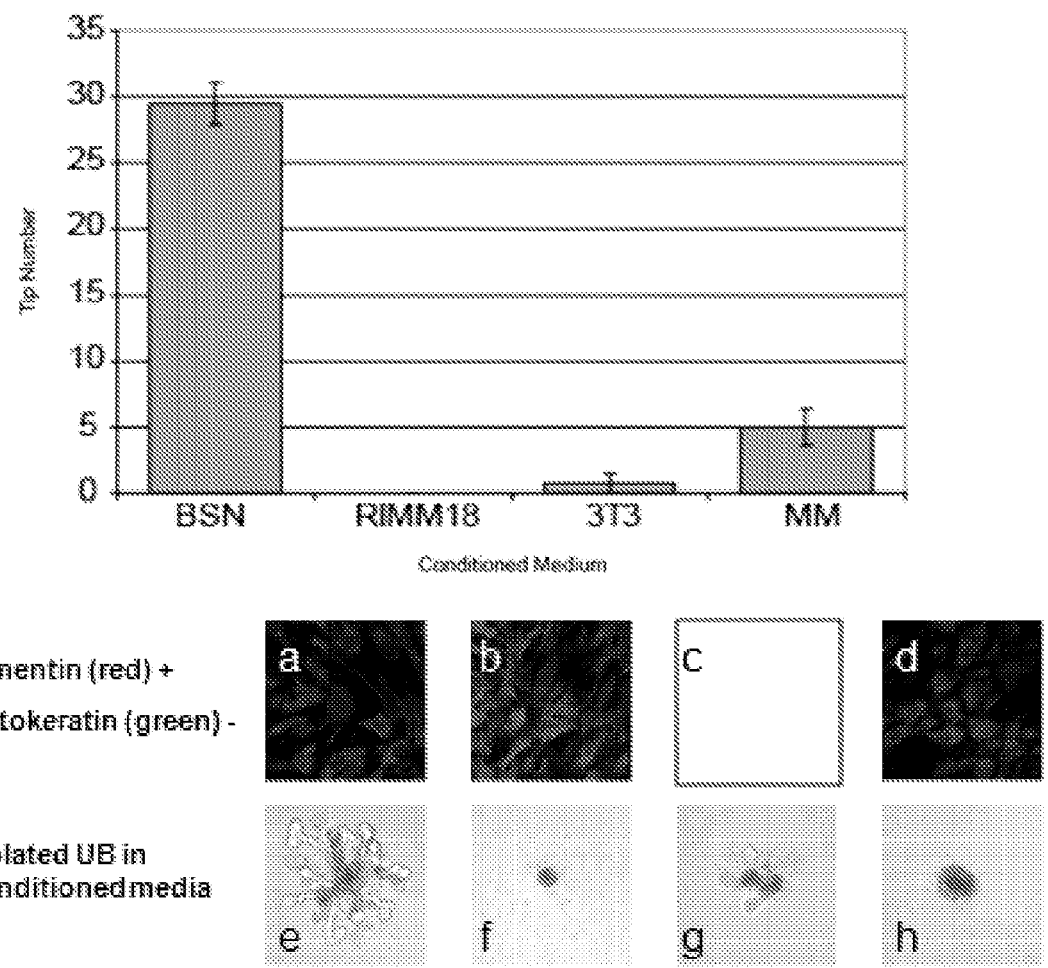
FIGS. 12A-H shows three MM derived cell lines were tested for the ability to induce isolated UB branching. The BSN (a), RIMM-18 (b), and MM primary (c) cell lines are all MM derived cell lines that are vimentin positive, cytokeratin negative. 3T3 fibroblasts (d) are also vimentin positive, cytokeratin negative cells, but are not MM derived. The conditioned medium from BSN cells strongly induced isolated UB branching (e) whereas the conditioned medium from primary MM cells slightly induced branching (g). The conditioned medium from RIMM-18 and 3T3 cells did not induce branching morphogenesis (f, h, respectively). Plot of tip number vs. cell-conditioned medium used (i) (ANOVA, P $\leq 0.00001$); *=P $\leq 0.05$, **=P $\leq 0.00005$. (50 μm—a,b,c,d; 250 μm scale bar—e,f,g,h).

In addition to a UB-like epithelial tubule, construction of a MM-like progenitor tissue derived from cultured cells would also be advantageous for the bio-engineering of kidney or kidney-like tissues. Therefore, it was investigated if any of the currently available cultured MM cells have the potential to substitute for the native progenitor tissue and whether the functions of the MM can be recapitulated by a homogenous cell line. Initially, three different MM-derived cell types (the well characterized BSN cell line, a conditionally immortalized metanephric mesenchymal cell line (RIMM-18), and primary rat E13 mM cells (which were found to be vimentin positive and cytokeratin negative, similar to the BSN cells and RIMM-18 cells (FIG. 12a-d)), as well as a 3T3 fibroblast cell line (as a control) were tested for their ability to secrete soluble factors capable of inducing isolated UB growth and branching. Of the media tested only that elucidated by BSN cells or by primary MM cells were capable of inducing isolated UB branching morphogenesis (FIG. 12,g); however, the BSN-CM was substantially more potent than the primary MM-CM (FIG. 12i). Although the RIMM-18 and 3T3 conditioned media did not induce UB branching, the 3T3-CM (which contains the branch-promoting factor, pleiotrophin appeared to induce slight globular growth of the isolated UB (FIG. 12h).

Experiments also shows that kidneys in the traditional filter culture grew flat and along the filter, while kidneys cultured in type I collagen or type IV collagen grew much thicker and in a more 3D manner.

A number of embodiments of the invention have been described. Nevertheless, it will be understood that various modifications may be made without departing from the spirit and scope of the invention. Accordingly, other embodiments are within the scope of the following claims.

What is claimed is:

1. A method of generating a tubular tissue structure, comprising:
    (a) contacting a Wolffian duct (WD) cell with GDNF and FGF1 to stimulate growth and proliferation;
    (b) contacting the cells with PTN and GDNF to promote formation of tubular tissue branches and/or globular morphology to generate a ureteric bud;
    (c) combining the ureteric bud tissue with metanephric mesenchyme in a biocompatible matrix; and
    (d) culturing the combination to form a tubular tissue or kidney tissue in vitro.

2. A method for in vitro culturing and propagating Wolffian duct bud tissue, comprising:
    isolating Wolffian duct bud tissue from mesenchyme tissue obtained from embryonic kidney rudiments;
    culturing the isolated Wolffian duct bud tissue in a biocompatible matrix in the presence of a culture medium comprising FGF1 and GDNF to produce tubular branches within the biocompatible matrix;
    separating the plurality of branch tips to generate bud fragments; and
    culturing each of the bud fragments in a biocompatible matrix with a culture medium comprising pleiotrophin.

* * * * *